US011802306B2

(12) United States Patent
McFarland et al.

(10) Patent No.: US 11,802,306 B2
(45) Date of Patent: Oct. 31, 2023

(54) HYBRIDIZATION IMMUNOPRECIPITATION SEQUENCING (HIP-SEQ)

(71) Applicants: The Charles Stark Draper Laboratory, Inc., Cambridge, MA (US); President and Fellows of Harvard College, Cambridge, MA (US)

(72) Inventors: Kirsty A. McFarland, Melrose, MA (US); Andrew P. Magyar, Arlington, MA (US); Ting Pang, Cambridge, MA (US); Michael Springer, Brookline, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 622 days.

(21) Appl. No.: 16/755,710

(22) PCT Filed: Oct. 12, 2018

(86) PCT No.: PCT/US2018/055689
§ 371 (c)(1),
(2) Date: Apr. 13, 2020

(87) PCT Pub. No.: WO2019/075383
PCT Pub. Date: Apr. 18, 2019

(65) Prior Publication Data
US 2021/0198726 A1    Jul. 1, 2021

Related U.S. Application Data

(60) Provisional application No. 62/572,240, filed on Oct. 13, 2017.

(51) Int. Cl.
*C12Q 1/6827*    (2018.01)
(52) U.S. Cl.
CPC ................. *C12Q 1/6827* (2013.01)
(58) Field of Classification Search
CPC ............... C12Q 1/6827; C12Q 1/6869; C12Q 2521/301; C12Q 2521/513; C12Q 2525/161
See application file for complete search history.

(56) References Cited

U.S. PATENT DOCUMENTS

| | | | | |
|---|---|---|---|---|
| 5,679,522 A | * | 10/1997 | Modrich | C12Q 1/6827 435/174 |
| 2006/0160102 A1 | * | 7/2006 | Fakhrai-Rad | C12Q 1/6827 435/6.12 |
| 2010/0285970 A1 | * | 11/2010 | Rose | C12Q 2521/514 506/2 |

FOREIGN PATENT DOCUMENTS

WO    WO 1993/020233 A1    10/1993
WO    WO 2013/074632 A1    5/2013

OTHER PUBLICATIONS

International Preliminary Report on Patentability, dated Apr. 23, 2020, from International Application No. PCT/US201 8/055689, filed on Oct. 12, 2018. 8 pages.
International Search Report and Written Opinion of the International Searching Authority, dated Dec. 6, 2018, from International Application No. PCT/US2018/055689, filed on Oct. 12, 2018. 14 pages.
Babon, J.J., et al., "The use of resolvases T4 Endonuclease VII and T7 Endonuclease I in mutation detection," Mol. Biotech., 23(1): 73-81 (2003).
Birkenbihl, et al., "Endonuclease VIII Has Two DNA-Binding Sites Each Composed from One N- and One C-Terminus Provided by Different Subunits of the Protein Dimer," EMBO Journal, 17(15): 4527-4534 (1998).
Cobb, A.M., et al., "Sequence-specific and DNA structure-dependent interactions of *Escherichia coli* MutS and human p53 with DNA," Analytical Biochemistry, 442(1): 51-61 (2013).
Declais, A.C., et al., "New Insight into the Recognition of Branched DNA Structure by Junction-Resolving Enzymes," Current Opinion in Structural Biology, 18: 86-95 (2008).
Declais, A.C., et al., "The Active Site of the Junction-resolving Enzyme T7 Endonuclease I," J. Mol. Bio., 307(4): 1145-1158 (2001).
Duckett, D.R., et al. "Binding of the Junction-resolving Enzyme Bacteriophage T7 Endonuclease I to DNA: Separation of Binding and Catalysis by Mutation," J. Mol. Bio., 246(1): 95-107 (1995).
Gasc, C., et al., "Revealing large metagenomics regions through long DNA fragment hybridization capture," Microbiome, 5(33): 1-10 (2017).
Giedroc, D.P., et al., "Gene 32 Protein, the Single-Stranded DNA Binding Protein from Bacteriophase T4, is a Zinc Metalloprotein," Proc. Natl. Acad. Sci., 83: 8452-8456 (1986).
Giraud-Panis, M.J., et al., "T4 Endonuclease VII, Importance of a histidine—aspartate cluster within the zinc-binding domain," J. Biol. Chem., 271(51): 33148-33155 (1996).
Giraud-Panis, M.J., et al., "The modular character of a DNA junction resolving enzyme: a zinc binding motif in T4 endonuclease VII," J. Mol. Biol, 252(5):, 596-610 (1995).
Goodman, S.D., et al., "Deformation of DNA During Site-Specific Recombination of Bacteriophase λ: Replacement of IHF Protein by HU Protein or Sequence-Directed Bends," Proc. Natl. Acad. Sci., 89: 11910-11914 (1992).
Hadden, J.M., et al. "Metal ions bound at the active site of the junction-resolving enzyme T7 endonuclease I," The EMBO Journal, 21(13): 3505-3515 (2002).
Hadden, J.M., et al., "Crystal Structure of the Holliday Junction Resolving Enzyme T7 Endonuclease I," Nature Structural Biology, 8(1): 62-67 (2001).
Hilton, B., et al., "A New Structural Insight into XPA-DNA Interactions," Biosci. Rep., 34: 831-840 (2014).
Joo, W., et al., "Structure of the FANCI-FANCD2 Complex: Insights into the Fanconi Anemia DNA Repair Pathway," Science, 333(6040): 312-316 (2011).
Kamashev, D., et al., "The Histone-Like Protein HU Binds Specifically to DNA Recombination and Repair Intermediates," EMBO Journal, 19(23): 6527-6535 (2000).

(Continued)

*Primary Examiner* — Narayan K Bhat
(74) *Attorney, Agent, or Firm* — HoustonHogle LLP

(57) ABSTRACT

Methods of detecting unknown genetic modifications in a DNA sample from an organism are disclosed.

39 Claims, 10 Drawing Sheets

Specification includes a Sequence Listing.

(56) References Cited

OTHER PUBLICATIONS

Kumar, C., et al., "ATP Binding and Hydrolysis by *Saccharomyces cerevisiae* Msh2-Msh3 Are Diffrentially Modulated by Mismatch and Double-Strand Break Repair DNA Substrates," DNA Repair (Amst.), 18: 18-30 (2014).
Li, F., et al., "Role of Saw1 in Rad1/Rad10 Complex Assembly at Recombination Intermediates in Budding Yeast," EMBO Journal, 32: 461-472 (2013).
Mon, H., et al., "Production and characterization of the celery mismatch endonuclease CEL II using *baulovirus*/silkworm expression system," Appl. Mircobiol. Biotecnol., 97 (15): 6813-6822 (2013).
Natrajan, G., et al., "Structures of *Escherichia coli* DNA Mismatch Repair Enzyme MutS in Complex with Different Mismatches: A Common Regonition Mode for Diverse Substrates," Nucleic Acids Research, 31(16): 4814-4821 (2003).
Parkinson, M.J., et al., "Catalytic and binding mutants of the junction-resolving enzyme endonuclease 1 of bacteriophage T7: the role of acid residues," Nucleic Acids Res., 27(2): 682-689 (1999).
Peng, R.H., et al., "Kamchatka Crab Duplex-Specific Nuclease-Mediated Transcriptome Substraction Method for Identifying Long cDNAs of Differentially Expressed Genes," Analytical Biochemistry, 372: 148-155 (2008).
Pimkin, M., et al., "Recombinant Nucleases CEL I from Celery and SP I from Spinach for Mutation Detection," BMC Biotechnology, 7(29): 1-8 (2007).
Pinkel, D., et al., "Comparative genomic hybridization," Annual Review of Genomics and Human Genetics, 6: 331-354 (2005).
Pohler, J.R., et al., "T4 Endonuclease VII selects and alters the structure of the four-way DNA junction; binding of a resolution-defective mutant enzyme," J.Mol.Biol., 260(5): 678-696 (1996).
Qiu, X., et al., "Duplex-Specific Nuclease-Mediated Bioanalysis," Trends in Biotechnology, 33(3): 180-188 (2015).
Raaijmakers, H., et al., "Conformational flexibility in T4 endonuclease VII revealed by crystallography: implications for substrate binding and cleavage," J. Mol. Biol., 308(2): 311-323 (2001).
Surtees, J.A., et al., "Mismatch Repair Factor MSH2-MSH3 Binds and Alters the Conformation of Branched DNA Structures Predicted to form During Genetic Recombination," J. Mol. Bio., 360(3): 523-536 (2006).
Swinger, K.K., et al., "IHF and HU: Flexible Architects of Bent DNA," Current Opinion in Structural Biology, 14: 28-35 (2004).
Till, B.J., et al. "Mismatch cleavage by single-strand specific nucleases," Nucleic Acid Res., 32(8): 2632-2641 (2004).
Tsuji, T., et al., "Development of a simple and highly sensitive mutation screening system by enzyme mismatch cleavage with optimized conditions for standard laboratories," Electrophoresis, 29(7): 1473-1483 (2008).
Vouillot, L., et al., "Comparison of T7E1 and Surveyor Mismatch Cleavage Assays to Detect Muations Triggered by Engineered Nucleases," G3, 5: 407-415 (2015).
Yang, B., et al., "Purification, cloning, and characterization of the CEL I Nuclease," Biochemistry, 39(13): 3533-3541 (2000).
Yang, W., "Structure and Mechanism of DNA Lesion Recognition," Cell Research, 18: 184-197 (2008).
Yang, Y., et al., "Determination of Protein-DNA Binding Constants and Specificities from Statistical Analyses of Single Molecules: MutS-DNA Interactions," Nucleic Acid Research, 33(13): 4322-4334 (2005).
Yang, Z., et al., "Specific and efficient binding of XPA to double-strand/single strand DNA junctions with 3'- and/or 5'-ssDNA branches," Biochemistry, 45(51): 15921-15930 (2006).
Youil, R., et al., "Screening for mutations by enzyme mismatch cleavage with T4 endonuclease VII," PNAS, 92(1): 87-91 (1995).

\* cited by examiner

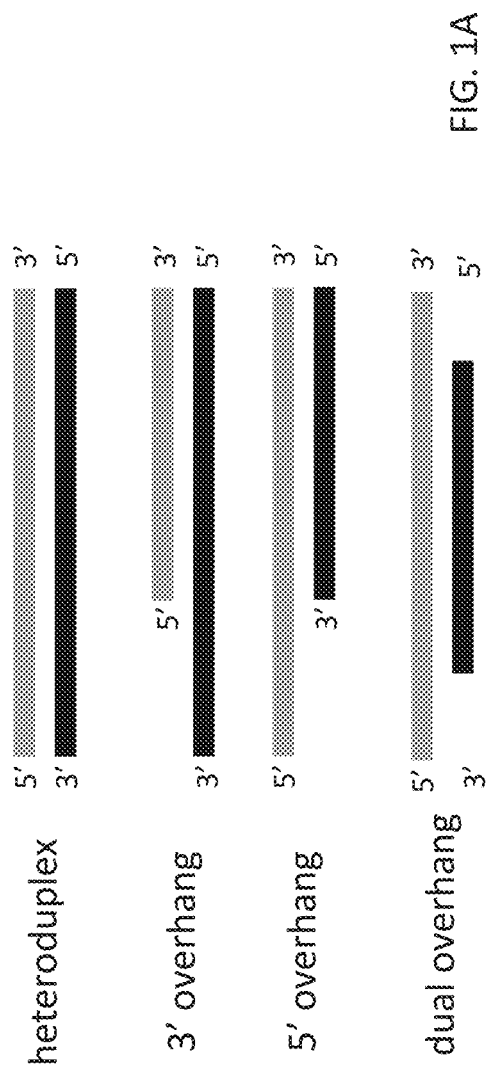
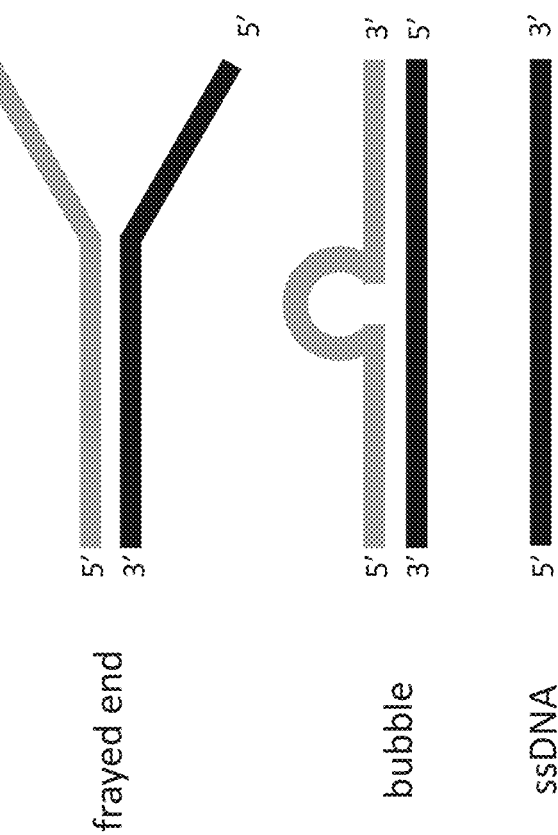
FIG. 1A
FIG. 1B

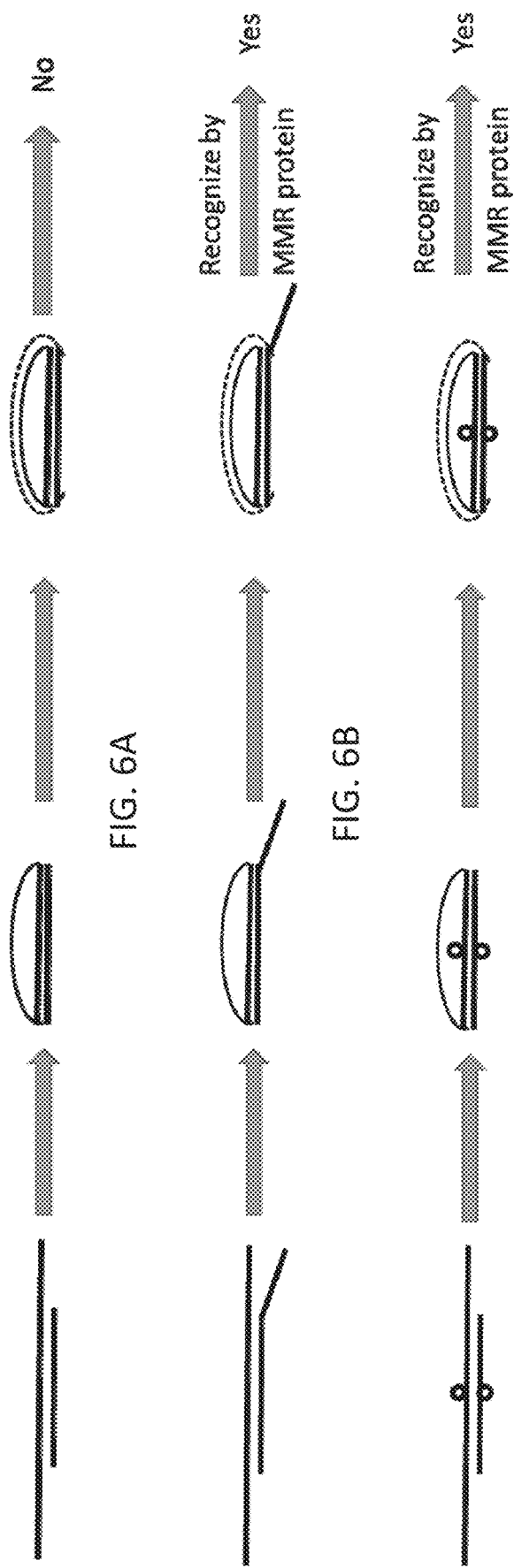

SEQ ID NO: 1

>NP_041972.1 endonuclease [Enterobacteria phage T7] (T7E1)

MAGYGAKGIRKVGAFRSGLEDKVSKQLESKGIKFEYEEWKVPYVIPASNHTYTPDFLLPNGIFVETKGLWESDDRKK
HLLIREQHPELDIRIVFSSSRTKLYKGSPTSYGEFCEKHGIKFADKLIPAEWIKEPKKEVPFDRLKRKGGKK

SEQ ID NO: 2

>WP_015969239.1 MULTISPECIES: recombination endonuclease VII [Bacteria] (T4E7)

MLLTGKLYKEEKQKFYDAQNGKCLICQRELNPDVQANHLDHDHELNGPKAGKVRGLLCNLCNAAEGQMKHKFN
RSGLKGQGVDYLEWLENLLTYLKSDYTQNNIHPNFVGDKSKEFSRLGKEEMMAEMLQRGFEYNESDTKTQLIASFK
KQLRKSLK

SEQ ID NO:3

>AAF42954.1 CEL I mismatch endonuclease [Apium graveolens]

MTRLYSVFFLLLALVVEPGVRAWSKEGHVMTCQIAQDLLEPEAAHAVKMLLPDYANGNLSSLCVWPDQIRHWYK
YRWTSSLHFIDTPDQACSFDYQRDCHDPHGGKDMCVAGAIQNFTSQLGHFRHGTSDRRYNMTEALLFLSHFMG
DIHQPMHVGFTSDMGGNSIDLRWFRHKSNLHHVWDREIILTAAADYHGKDMHSLLQDIQRNFTEGSWLQDVES
WKECDDISTCANKYAKESIKLACNWGYKDVESGETLSDKYFNTRMPIVMKRIAQGGIRLSMILNRVLGSSADHSLA

SEQ ID NO:4

>BAM38525.1 endonuclease [Apium graveolens] (CEL II)

MGMLTYTGIYFLLLLPSVFCWGKQGHFAICKIAQGFLSKDALTAVKALLPEYADGDLAAVCSWADEVRFHMRWSS
PLHYVDTPDFRCNYKYCRDCHDSVGRKDRCVTGAIHNYTEQLLLGVHDLNSKMNNNLTEALMFLSHFVGDVHQP
LHVGFLGDEGGNTITVRWYRRKTNLHHVWDTMMIESSLKTFYNSDLSSLIQAIQSNITGVWLTDSLSWSNCTADH
VVCPDPYASESIELACKFAYRNATPGTTLGDEYFLSRLPVAEKRLAQAGVRLAATLNRIFTSNPSDLTRLNMHNGGH
RSSNNIEIV

FIG. 7A

SEQ ID NO: 5

>WP_001272928.1 MULTISPECIES: DNA mismatch repair protein MutS [Proteobacteria]

MSAIENFDAHTPMMQQYLRLKAQHPEILLFYRMGDFYELFYDDAKRASQLLDISLTKRGASAGEPIPMAGIPYHAV
ENYLAKLVNQGESVAICEQIGDPATSKGPVERKVVRIVTPGTISDEALLQERQDNLLAAIWQDSKGFGYATLDISSGR
FRLSEPADRETMAAELQRTNPAELLYAEDFAEMSLIEGRRGLRRRPLWEFEIDTARQQLNLQFGTRDLVGFGVENA
PRGLCAAGCLLQYAKDTQRTTLPHIRSITMEREQDSIIMDAATRRNLEITQNLAGGAENTLASVLDCTVTPMGSRM
LKRWLHMPVRDTRVLLERQQTIGALQDFTAGLQPVLRQVGDLERILARLALRTARPRDLARMRHAFQQLPELRAQ
LETVDSAPVQALREKMGEFAELRDLLERAIIDTPPVLRDGGVIASGYNEELDEWRALADGATDYLERLEVRERERT
GLDTLKVGFNAVHGYYIQISRGQSHLAPINYMRRQTLKNAERYIIPELKEYEDKVLTSKGKALALEKQLYEELFDLLLP
HLEALQQSASALAELDVLVNLAERAYTLNYTCPTFIDKPGIRITEGRHPVVEQVLNEPFIANPLNLSPQRRMLIITGPN
MGGKSTYMRQTALIALMAYIGSYVPAQKVEIGPIDRIFTRVGAADDLASGRSTFMVEMTETANILHNATEYSLVLM
DEIGRGTSTYDGLSLAWACAENLANKIKALTLFATHYFELTQLPEKMEGVANVHLDALEHGDTIAFMHSVQDGAA
SKSYGLAVAALAGVPKEVIKRARQKLRELESISPNAAATQVDGTQMSLLSVPEETSPAVEALENLDPDSLTPRQALE
WIYRLKSLV

SEQ ID NO:6

>NP_014551.1 mismatch repair ATPase MSH2 [Saccharomyces cerevisiae S288C]

MSSTRPELKFSDVSEERNFYKKYTGLPKKPLKTIRLVDKGDYYTVIGSDAIFVADSVYHTQSVLKNCQLDPVTAKNFH
EPTKYVTVSLQVLATLLKLCLLDLGYKVEIYDKGWKLIKSASPGNIEQVNELMNMNIDSSIIIASLKVQWNSQDGNCII
GVAFIDTTAYKVGMLDIVDNEVYSNLESFLIQLGVKECLVQDLTSNSNAEMQKVINVIDRCGCVVTLLKNSEFSE
KDVELDLTKLLGDDLALSLPQKYSKLSMGACNALIGYLQLLSEQDQVGKYELVEHKLKEFMKLDASAIKALNLFPQGP
QNPFGSNNLAVSGFTSAGNSGKVTSLFQLLNHCKTNAGVRLLNEWLKQPLTNIDEINKRHDLVDYLIDQIELRQML
TSEYLPMIPDIRRLTKKLNKRGNLEDVLKIYQFSKRIPEIVQVFTSFLEDDSPTEPVNELVRSVWLAPLSHHVEPLSKFE
EMVETTVDLDAYEENNEFMIKVEFNEELGKIRSKLDTLRDEIHSIHLDSAEDLGFDPDKKLKLENHHLHGWCMRLTR
NDAKELRKHKKYIELSTVKAGIFFSTKQLKSIANETNILQKEYDKQQSALVREIINITLTYTPVFEKLSLVLAHLDVIASFA
HTSSYAPIPYIRPKLHPMDSERRTHLISSRHPVLMQDDISFISNDVTLESGKGDFLIITGPNMGGKSTYIRQVGVISL
MAQIGCFVPCEEAEIAIVDAILCRVGAGDSQLKGVSTFMVEILETASILKNASKNSLIIVDELGRGTSTYDGFGLAWAI
AEHIASKIGCFALFATHFHELTELSEKLPNVKNMHVVAHIEKNLKEQKHDDEDITLLYKVEPGISDQSFGIHVAEVVQ
FPEKIVKMAKRKANELDDLKTNNEDLKKAKLSLQEVNEGNIRLKALLKEWIRKVKEEGLHDPSKITEEASQHKIQELL
RAIANEPEKENDNYLKYIKALLL

FIG. 7B

SEQ ID NO:7

>NP_010016.2 mismatch repair protein MSH3 [Saccharomyces cerevisiae S288C]

MAGQPTISRFFKKAVKSELTHKQEQEVAVGNGAGSESICLDTDEEDNLSSVASTTVTNDSFPLKGSVSSKNSKNSEK
TSGTSTTFNDIDFAKKLDRIMKRRSDENVEAEDDEEEGEEDFVKKKARKSPTAKLTPLDKQVKDLKMHHRDKVLVIR
VGYKYKCFAEDAVTVSRILHIKLVPGKLTIDESNPQDCNHRQFAYCSFPDVRLNVHLERLVHHNLKVAVVEQAETSA
IKKHDPGASKSSVFERKISNVFTKATFGVNSTFVLRGKRILGDTNSIWALSRDVHQGKVAKYSLISVNLNNGEVVYDE
FEEPNLADEKLQIRIKYLQPIEVLVNTDDLPLHVAKFFKDISCPLIHKQEYDLEDHVVQAIKVMNEKIQLSPSLIRLVSKL
YSHMVEYNNEQVMLIPSIYSPFASKIHMLLDPNSLQSLDIFTHDGGKGSLFWLLDHTRTSFGLRMLREWILKPLVDV
HQIEERLDAIECITSEINNSIFFESLNQMLNHTPDLLRTLNRIMYGTTSRKEVYFYLKQITSFVDHFKMHQSYLSEHFKS
SDGRIGKQSPLLFRLFSELNELLSTTQLPHFLTMINVSAVMEKNSDKQVMDFFNLNNYDCSEGIIKIQRESESVRSQL
KEELAEIRKYLKRPYLNFRDEVDYLIEVKNSQIKDLPDDWIKVNNTKMVSRFTTPRTQKLTQKLEYYKDLLIRESELQY
KEFLNKITAEYTELRKITLNLAQYDCILSLAATSCNVNYVRPTFVNGQQAIIAKNARNPIIESLDVHYVPNDIMMSPEN
GKINIITGPNMGGKSSYIRQVALLTIMAQIGSFVPAEEIRLSIFENVLTRIGAHDDIINGDSTFKVEMLDILHILKNCNK
RSLLLLDEVGRGTGTHDGIAISYALIKYFSELSDCPLILFTTHFPMLGEIKSPLIRNYHMDYVEEQKTGEDWMSVIFLYK
LKKGLTYNSYGMNVAKLARLDKDIINRAFSISEELRKESINEDALKLFSSLKRILKSDNITATDKLAKLLSLDIH

SEQ ID NO:8

>KZV12333.1 MSH6 [Saccharomyces cerevisiae]

MAPATPKTSKTAHFKNGSTSSQKKMKQSSLLSFFSKQVPSGTPSKKVQKPTPATLENTATDKITKNPEGGKTGKLFV
DADEDNDLTIAEETVSTVRSDIMHSQEPQSDTMLNSNTTEPKSTTTDEDLSSSQSRRNHKRRLNYAESDDDDSDTT
FTAKRKKGKVVDSESDEDEYLPDKNDGDEDDDIADDKEDIKGELAEDSGDDDDLISLAETTSKKKFSYNTSHSSSPFT
RNISRNNSKKKSRPNQAPSRSYNPSHSQPSATSKSSKFNKQNEERYQWLVDERDAQRRPKSDPEYDPRTLYIPSSA
WNKFTPFEKQYWEIKSKMWDCIVFFKKGKFFELYEKDALLANALFDLKIAGGGRANMQLAGIPEMSFEYWAAQFI
QMGYKVAKVDQRESMLAKEMREGSKGIVKRELQCILTSGTLTDGDMLHSDLATFCLAIREEPGNFYNETQLDSSTI
VQKLNTKIFGAAFIDTATGELQMLEFEDDSECTKLDTLMSQVRPMEVVMERNNLSTLANKIVKFNSAPNAIFNEVK
AGEEFYDCDKTYAEIISSEYFSTEEDWPEVLKSYYDTGKKVGFSAFGGLLYYLKWLKLDKNLISMKNIKEYDFVKSQHS
MVLDGITLQNLEIFSNSFDGSDKGTLFKLFNRAITPMGKRMMKKWLMHPLLRKNDIESRLDSVDSLLQDITLREQLE
ITFSKLPDLERMLARIHSRTIKVKDFEKVITAFETIIELQDSLKSNDLKGDVSKYISSFPEGLVEAVKSWTNAFERQKAIN
ENIIVPQRGFDIEFDKSMDRIQELEDELMEILMTYRKQFKCSNIQYKDSGKEIYTIEIPISATKNVPSNWVQMAANKT
YKRYYSDEVRALARSMAEAKEIHKTLEEDLKNRLCQKFDAHYNTIWMPTIQAISNIDCLLAITRTSEYLGAPSCRPTIV
DEVDSKTNTQLNGFLKFKSLRHPCFNLGATTAKDFIPNDIELGKEQPRLGLLTGANAAGKSTILRMACIAVIMAQM
GCYVPCESAVLTPIDRIMTRLGANDNIMQGKSTFFVELAETKKILDMATNRSLLVVDELGRGGSSSDGFAIAESVLH
HVATHIQSLGFFATHYGTLASSFKHHPQVRPLKMSILVDEATRNVTFLYKMLEGQSEGSFGMHVASMCGISKEIID
NAQIAADNLEHTSRLVKERDLAANNLNGEVVSVPGGLQSDFVRIAYGDGLKNTKLGSGEAVLNYDWNIKRNVLKS
LFSIIDDLQS

FIG. 7C

SEQ ID NO: 9

>NP_009375.1 DNA-binding protein SAW1 [Saccharomyces cerevisiae S288C]

MAPSIATVKIARDMVLPLRIFVNRKQILQTNDKTSNKSNATIFEAPLLSNNSIICLKSPNTRIYLSQQDKKNLCDEIKED
LLLIVYELASPEIISSVLSKIRVGHSTDFQINVLPKLFAGADTDNAVTSHIQSVTRLAKFKYKLHYKHKWELDIFINSIKKI
ANLRHYLMFQTLTLNGFSLNAGPKTLLARKIEKQPQVPNLLIENGDA

SEQ ID NO:10

> XPA: DNA repair protein complementing XP-A cells isoform 2 [Homo sapiens], NCBI Reference Sequence: NP_001341904.1

MFILTPKLQIPATFDGMANVKAAPKIIDTGGGFILEEEEEEEQKIGKVVHQPGPVMEFDYVICEECGKEFMDSYLMN
HFDLPTCDNCRDADDKHKLITKTEAKQEYLLKDCDLEKREPPLKFIVKKNPHHSQWGDMKLYLKLQIVKRSLEVWG
SQEALEEAKEVRQENREKMKQKKFDKKVKELRRAVRSSVWKRETIVHQHEYGPEENLEDDMYRKTCTMCGHELT
YEKM

FIG. 7D

HYBRIDIZATION IMMUNOPRECIPITATION SEQUENCING (HIP-SEQ)

RELATED APPLICATIONS

This application is a § 371 National Phase Application of International Application No. PCT/US2018/055689 filed on Oct. 12, 2018, now International Publication No. WO 2019/075383, published on Apr. 18, 2019, which International Application claims the benefit under 35 U.S.C. § 119(e) of U.S. Provisional Application No. 62/572,240, filed on Oct. 13, 2017, both of which are incorporated herein by reference in their entirety.

GOVERNMENT SUPPORT

This invention was made with Government support under contract number N6600118C4503, awarded by IARPA. The Government has certain rights in the invention.

INCORPORATION BY REFERENCE OF MATERIAL IN ASCII TEXT FILE

The instant application contains a Sequence Listing which has been filed electronically in ASCII format and is hereby incorporated by reference in its entirety. Said ASCII copy, created on Oct. 12, 2018, is named 0352_0043WO1_SL.txt and is 47,540 bytes in size.

BACKGROUND OF THE INVENTION

Identification of genetic changes that exist in small subpopulations of cells or organisms is important for a variety of applications including the identification of engineered organisms in the environment, identifying sequences associated with cancer or other diseases, or identifying off-target effects of gene editing. Whole genome analysis by next generation sequencing (NGS) can provide an accurate means to identify insertions/deletions (indels) of particular genes, or mutations down to single nucleotide polymorphisms (SNPs). However, if there is a single engineered organism (e.g., a mosquito) in a sample of hundreds of organisms/mosquitos, the sequence associated with the genetic change can be lost in the background of the unmodified organisms.

The ability to selectively capture and enrich sequences associated with unknown genetic modifications, either natural or engineered, will dramatically reduce the sequencing costs required to identify rare changes, and in certain situations enable the identification genetic changes that are currently not detectable.

SUMMARY OF THE INVENTION

The present invention encompasses methods of identifying or detecting the presence of, or absence of, genetic modifications (also referred to herein as mutations) in a sample comprising nucleic acids. In particular, the sample (e.g., a genomic DNA sample) is obtained from an organism and the genetic modifications can encompass insertions, deletions (also referred to herein as indels) as well as single nucleotide polymorphisms (SNPs). The sample can also be any sample containing nucleic acids such as DNA or RNA. In particular, the genetic modifications are not previously known, that is, the genetic modifications are not normally present in the DNA of the reference (i.e., normal organism).

In particular, the sample is a sample from a prokaryotic or eukaryotic organism of interest, or a virus. Prokaryotic organisms, for example, are bacteria, and eukaryotic organisms can include yeasts, fungi, protozoa, algae, plants or animals. As encompassed herein, animals include mammals, and specifically include humans. Viruses can be DNA or RNA viruses.

For example, cells can be obtained from a human wherein the cells comprise DNA, such as blood cells, epithelial cells, saliva, cerebral spinal fluid, or other bodily fluids containing DNA such as sweat, feces or tears.

The sample can be enriched to capture target DNA, such as genomic DNA, obtained from the organism. Such techniques known as genomic fragment enrichment (GFE) can be used to obtain regions/segments of target DNA that is of suitable size/length to specifically hybridize with capture probes (non-overlapping probes) to allow enrichment of large genomic regions of the genome (such as about 1 kb fragments up to about tens of kilobases with short, non-overlapping probes specific to a particular DNA (e.g., gene) sequence. After enrichment the target DNA can be fragmented to allow for further assay.

After enrichment, the fragmented target DNA is contacted with (incubated with) labelled capture probes under conditions suitable for specific hybridization with the target DNA. The capture probes are generated from reference/cognate DNA, without any genetic variation (e.g., native or unmodified DNA). These reference/cognate probes hybridize with the target DNA resulting in a mixture of hybridization products including cognate probes hybridized with DNA comprising substantially complementary sequence matches (substantial complementarity) of the target DNA forming match duplex structures as described herein; cognate probes hybridizing, or partially hybridizing with mismatched sequences (e.g., non-complementary sequences for example with genetic modifications such as insertions, deletions or polymorphisms) of the target DNA forming mismatch duplex structures as described herein, and unhybridized ssDNA. As described herein, mismatch duplex structures (i.e., mismatched probe/target DNA structures) can comprise frayed ends, bubbles, cruciform structures and Holliday structures and junctions. As described herein, the term "mismatch duplex structures" are structures associated with genetic modifications and comprise the aforementioned mismatched structures.

The cognate probes can be labelled with a detectable label such as biotin, or other suitable label as known to those of skill in the art. The cognate probes are labelled, resulting in labelled match duplex structures and mismatch duplex structures in the hybridization mixture. The conditions of hybridization such as stringency conditions (buffers, temperature and time) are known to those of skill in the art and can be optimized for specific assays.

To separate the mismatched hybridization products comprising labelled probe and target DNA from the match duplex structures or unhybridized DNA in the hybridization mixture, the mixture is contacted with and allowed to specifically react with or bind to, one, or more proteins capable of specifically binding to or recognizing the mismatched hybrid products of the mixture (also referred to herein as "mismatch recognition proteins"). Such proteins include endonucleases, mismatch or DNA repair proteins, or DNA binding proteins as described herein. In particular, such proteins can be, for example, endonucleases from e.g., bacteriophages such as T7E, T4E7, CEL I or CEL II. Other proteins encompassed by the present invention are DNA mismatch repair proteins such as MutS, MSH2, MSH3 and MSH6, or DNA binding proteins such as SAW1 or XP-A (SEQ ID NOS:1-10). Any combination or cocktail of endonucleases, DNA repair/binding proteins can be used in the methods of the present invention. For example one, or more endonucleases can be used with one, or more DNA repair proteins. The proteins e.g., the endonucleases, can be genetically engineered as described herein to completely, or partially abrogate the catalytic activity (i.e., enzymatic digestion) allowing the proteins to bind to the heteroduplexes but not digest/destroy the target DNA. Additional modifications can be engineered into the proteins to increase binding activity, affinity or specificity. The proteins can be fulllength, or can be shorter fragments and can also include other modifications/variations that do not interfere with the ability of the protein to specifically interact with the DNA of the mismatched structures.

In a particular embodiment of the present invention the protein is tagged with an affinity tag/label, such as a histidine tag. Other suitable tags can be used, and alternative affinity tags are well-known to those of skill in the art. As described herein, the protein(s) are incubated with the duplex structures under conditions for the protein to specifically interact with the mismatched products of the hybridization mixture to form affinity-tagged protein/mismatch duplex structure complexes.

To recover the protein/mismatch duplex structure complex, the complexes can be cross-linked (e.g., chemically cross-linked) and purified by immunoprecipitation techniques using an antibody, or an antibody fragment, that specifically recognizes/binds to the affinity tag of the protein, thereby selectively identifying and isolating/obtaining only those target DNA fragments that contain a mismatch. After immunoprecipitation, the mismatched target DNA can be selectively separated from the capture probe. For example, if the capture probe is labelled with biotin, the biotinylated probes can be immobilized onto magnetic streptavidin beads and exposed to denaturing conditions as known to those of skill in the art, thereby separating double stranded DNA and releasing the mismatched target DNA from the probe immobilized on the bead. After centrifugation, the supernatant will contain the mismatched target DNA, and the supernatant can be further processed for optional amplification (e.g., PCR) and sequencing (e.g. paired-end sequencing) using known methods. Sequencing the target DNA will determine/confirm if a genetic modification is present or absent in the target DNA, and the location of the modification in the DNA/genomic sequence.

Additional steps can be taken to analyze the unhybridized DNA (i.e., ssDNA not hybridized to a capture probe). Unhybridized DNA and hybridized matched duplex DNA can be present in the supernatant after the immunoprecipitation step. The matched DNA is bound to the labelled capture probe, typically labeled with biotin. As described herein, the probe/matched DNA duplex can be immobilized on streptavidin coated magnetic beads and the unhybridized DNA remaining in the supernatant can be recovered, optionally amplified and sequenced.

As a result of the present invention, methods are now available to identify unknown insertions, deletions and single nucleotide polymorphisms in a DNA sample from a known organism. These methods can be particularly useful to identify an organism whose DNA (e.g., genomic DNA) has been genetically engineered using comparative genomic hybridization and chromatin immunoprecipitation techniques. More particularly, these methods have the potential to identify engineered genetic modification even from a complex mixture of organisms.

The above and other features of the invention including various novel details of construction and combinations of parts, and other advantages, will now be more particularly described with reference to the accompanying drawing and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 1 depicts different structures that result from hybridization of a reference genome (gray) with sample DNA (black). FIG. 1A shows structures that occur in regions of homology between the sample and reference while FIG. 1B shows structures from regions that differ between the sample and reference.

FIG. 6A-C shows a work flow diagram for eliminating sequences with overhangs that are not indicative of genetic differences between the sample and the reference genome, but may be recognized by certain mismatch recognition proteins.

FIG. 7A-D show the sequences (SEQ ID NOS; 1-10) of the endonuclease, mismatch repair, DNA binding and DNA repair proteins described herein.

DETAILED DESCRIPTION OF THE PREFERRED EMBODIMENTS

Figure 2:
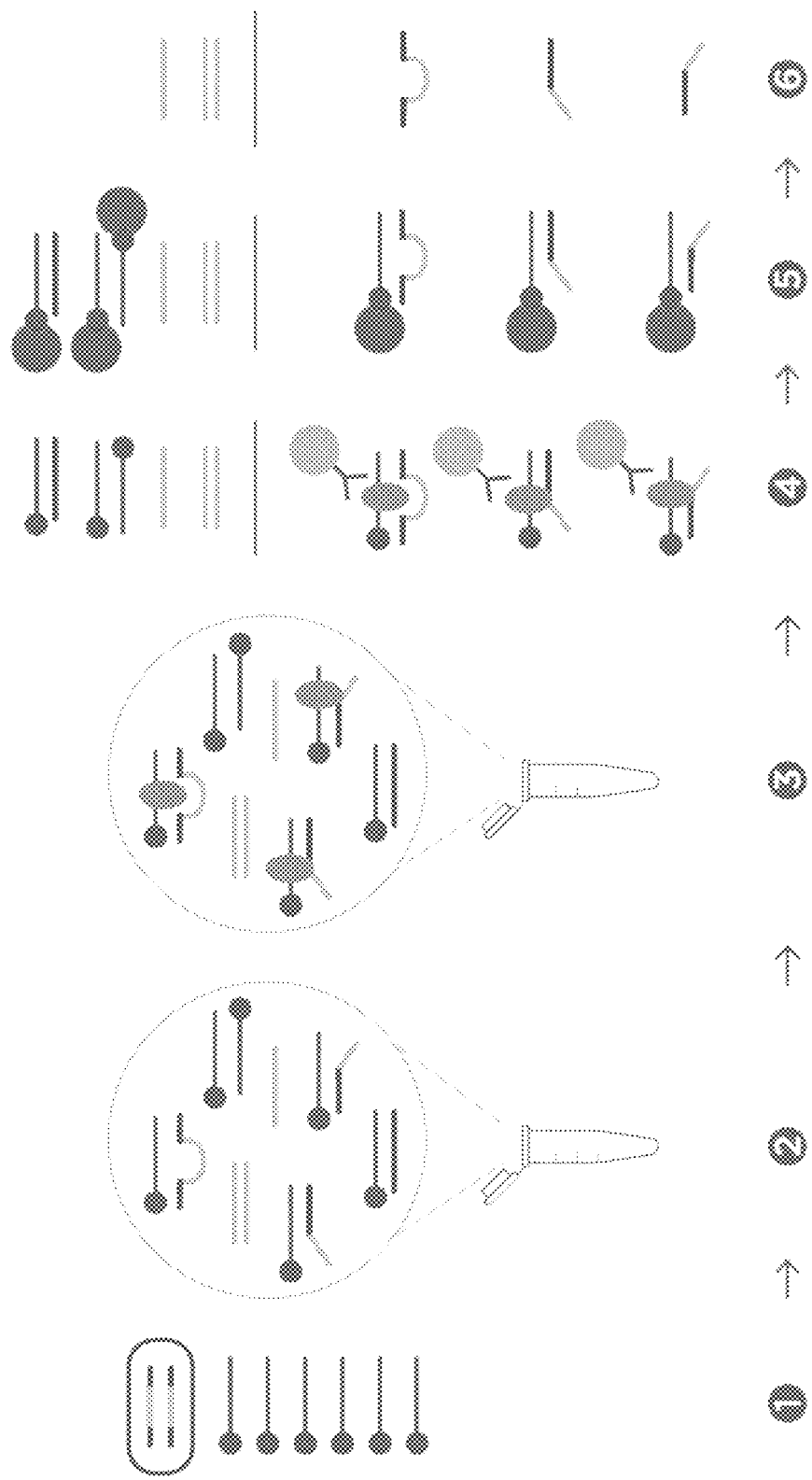
FIG. 2 shows the steps (2-1 through 2-6) of the method as described herein to capture and partition DNA sequences possessing genetic alterations from a reference genome.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Techniques such as comparative genomic hybridization have been used to identify genomic variations between organisms. In comparative genomic hybridization, DNA from a reference genome is hybridized to sample DNA. Fluorescence-based assays are then used to identify variations in copy-number between the two samples. ("Comparative genomic hybridization", Annual Review of Genomics and Human Genetics, 2005 Sep. 22, 6, 331-354) Comparative genomic hybridization does not enable the detection of insertions of genes from other organisms and is limited to changes that are 200 nt or larger.

As described herein, in methods of the present invention, sample DNA is hybridized to a reference genome and then specialized proteins are used to identify and capture DNA associated with mismatches between the sample and the references. When the reference genome DNA is hybridized to the sample DNA a variety of possible DNA structures can result. In regions where the DNA is a match (FIG. 1A), either a heteroduplex or structures with a 3'- and/or 5'-overhang are generated. In regions where there is a difference between the reference and sample genome, such as from an indel, the DNA will not properly hybridize. As a result, specific DNA structures such as a frayed end or bubble (FIG. 1B) will result, or the DNA will not hybridize to the reference at all leaving an unpaired ssDNA segment, or a dsDNA sample pair.

Novel methods are described herein that use mismatch recognition proteins known to specifically recognize/bind to particular DNA structures to capture and enrich sequences associated with insertions or deletions or SNPs (i.e., mismatched DNA). This subset of mismatched DNA can be sequenced, enabling identification and location of the specific genetic modifications.

The method uses nucleic acid probes designed to recognize a known organism that may contain an unknown modification. This approach has the potential to identify engineering or other modifications even in a complex background/mixture of unknown organisms. Additionally, the methods encompassed herein permit successive testing on samples, allowing probing for additional genetic information. The capture probes will hybridize to known genomic targets in the sample of interest. Probes interacting with complementary targets will have substantially complementary or exact duplexes, whereas those containing regions of non-complementarity will lead to changes in duplex structure. These structures can be identified and purified using specialized proteins recognizing structures indicative of mismatched DNA duplexes. Additionally, the method preserves sample targets having no regions of identity with the reference, enabling the sequencing or further processing of this DNA. The modification-containing DNA can be partitioned and prepared for sequencing, allowing identification of both the modification and its genomic location/junctions. For example, methods described herein can also identify locations of CRISPR-mediated genome changes, particularly when assessing off-target CRISPR effects, Current technology only permits analyzing known target regions, whereas the methods described herein can assess genome-wide changes.

The method for capture and enrichment of regions of genetic alteration is shown in FIG. 2 and described below.

Probe generation. A library of probes (FIG. 2-1) is generated from the reference genome of the organism of interest. The probes are labelled by incorporation of a label such as a biotin moiety during probe synthesis, thereby facilitating the purification of the target DNA samples at a later step in the workflow.

Hybridization with genomic sample (FIG. 2-2) The initial enriched DNA of interest is fragmented and mixed with the labelled probes in a hybridization reaction to allow the capture probes to interact and hybridize/anneal with the sample DNA. If the reference genome fragments are a perfect match to their cognate probes, there should mostly exist a perfect complement (i.e., a match duplex structure). In the presence of a mismatch or SNP, in some cases there may be a change in the structure of the DNA duplex (a mismatch duplex structure); this would also be the case for heteroduplexes that contain an insertion or deletion.

Figure 3C:
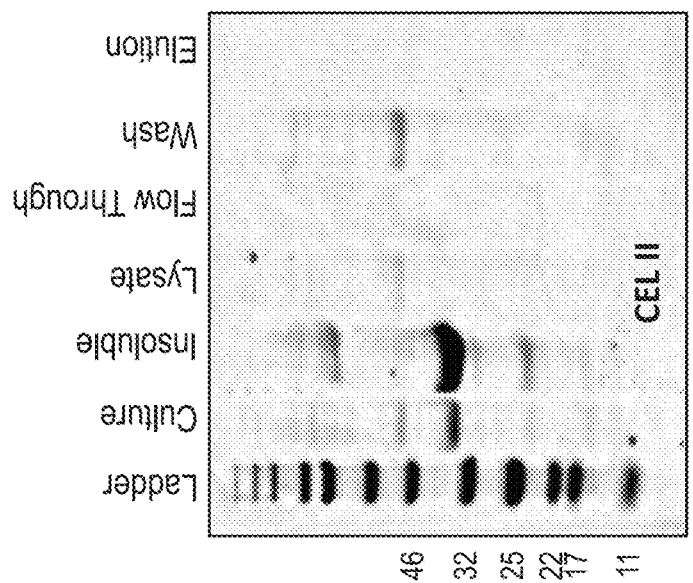
FIG. 3 depicts protein gel electrophoresis showing production of recombinant T7E1 (FIG. 3A), T4E7 (FIG. 3B), and CELII (FIG. 3C). All three proteins are engineered to contain a 6×-His-tag that can be used both for purification and for immunoprecipitation of enzyme-DNA complexes. The protein gels show successful affinity purification of both T7E1 and T4E7 using the His-tag.

Recognition of mismatches (FIG. 2-3) Proteins that can recognize these mismatched structures are used to specifically purify regions of DNA possessing non-complementarity to their cognate probes. A single mismatch recognition protein, or a mixture/cocktail of proteins can be used. The protein or protein cocktail is incubated with the hybridized capture probe-sample DNA mix, allowed to interact with their target structure, and chemically cross-linked with their structural target, in vitro.

Immunoprecipitation of mismatches (FIG. 2-4) The proteins used to recognize the mismatches are engineered to contain an affinity tag. This affinity tag is used to purify the crosslinked DNA-protein complexes by immunoprecipitation using antibodies against the affinity tag. This step selectively isolates or purifies only the fragments that contain a mismatch to their cognate probe.

Release of mismatch fragments of interest (FIG. 2-5) After immunoprecipitation to selectively isolate/purify only those fragments that contain a mismatch, the mismatched DNA must be separated from the capture probe. To do this, the biotinylated probes are immobilized onto a streptavidin-coated magnetic bead, the DNA samples are denatured using standard techniques to allow separation of the two strands followed by retention of the magnetic beads, and removal of the supernatant that now contains only the mismatched sample fragments. The mismatched samples are prepared for paired-end sequencing, following an optional amplification step.

Partition of unhybridized DNA sample. (FIG. 2-6) The immunoprecipitation step allows partitioning of the sample, selectively isolating/purifying the mismatched DNA from the sample, while leaving unhybridized DNA that does not find a match (as well as the perfectly-match sample) free in the supernatant. Unhybridized sample DNA that was not purified directly by the IP, but that contains an entirely different sequence to the hybridization probes and is therefore of interest, may be isolated/purified from the supernatant. As the perfectly-match DNA is biotinylated, whereas the unhybridized sample DNA is not, the perfect match DNA can be purified away from the unhybridized DNA using a streptavidin-coated magnetic bead. Unhybridized DNA samples can be purified and prepared for sequencing.

DNA Structural Recognition Proteins

There exist many naturally occurring proteins that are known to recognize particular DNA structures. These proteins are candidates for the recognition and capture of DNA mismatches, either in their native state, with protein engineering, or by modifying the solution in which the DNA and proteins interact. In biological organisms, inherent errors occur at known frequencies during DNA replication and other genetic transactions. To prevent detrimental effects of mistakes, most organisms contain proteins whose functions are to recognize and correct for errors. In addition, bacteriophages are known to contain specialized proteins (nuclease enzymes) that function to resolve specific structures that form during viral DNA insertion into the bacterial chromosome, by recognizing and digesting the DNA structure, which is then repaired by other cellular proteins. Some specialized proteins have been exploited by biotechnology and are commercially available for in vitro use, where they can be applied to recognize and degrade DNA containing those specific structures. ("The use of resolvases T4 Endonuclease VII and T7 Endonuclease I in mutation detection", Mol. Biotech. 2003, 23, 73-81; "Screening for mutations by enzyme mismatch cleavage with T4 endonuclease VII", PNAS, 1995 January, 92, 87-91; "Comparison of T7E1 and Surveyor Mismatch Cleavage Assays to Detect Mutations Triggered by Engineered Nucleases". G3, 2015 Mar. 5, 407-415; "Mismatch cleavage by single-strand specific nucleases". NAR, 2004, 32:8, 2632-2641) T7 bacteriophage endonuclease 1 (T7E1) is one such structure-selective enzyme: it can recognize mismatched DNA, cruciform DNA structures, Holliday structures or junctions and can accurately recognize insertions and deletions of ≥2 bases. Mismatches in hybridization can manifest in numerous ways: SNPs, insertions, and deletions in DNA that hybridize or partially hybridize to capture probes will cause particular duplex structures to occur that are normally associated with error formation. It is possible to utilize enzymes like T7E1 to detect and interact with the structures, which would then be digested by the protein's nuclease/enzymatic activity.

Through targeted mutation of enzymes such as T7E1, engineered enzyme variants DNA structures associated with mismatches can be recognized, but not digested. In general, the mechanism and location of the key catalytic amino acids of these nucleases are known, and these residues can be substituted to disable the protein's catalytic activity, while preserving the ability of the protein to detect the structural change. Engineered proteins are expressed with an affinity tag to allow purification and detection.

T7 endonuclease 1 (T7E1) (SEQ ID NO:1): Endonuclease I is encoded by the bacteriophage T7 and is able to selectively bind and cleave four-way DNA-junctions. ("Catalytic and binding mutants of the junction-resolving enzyme endonuclease 1 of bacteriophage T7: the role of acid residues", NAR, 1999, 27:2, 682-689; "The Active Site of the Junction-resolving Enzyme T7 Endonuclease I", J. Mol. Bio., 2001, 307, 1145-1158). The T7E1 enzyme is commonly used in a commercially available, mismatch cleavage assay (NEB) to detect mutations. As reported by Tsuji et al., ("Development of a simple and highly sensitive mutation screening system by enzyme mismatch cleavage with optimized conditions for standard laboratories", Electrophoresis, 2008, 29). T7E1 is able to detect insertions or deletions between 1-18 nt in length as well as some single base substitutions by characterizing cleavage of DNA by gel electrophoresis.

To use of T7E1 to capture and enrich sequences with genetic modifications the nuclease activity can be inhibited by several different means. Metal ions, such as Mn or Mg or Zn are required for catalytic activity of T7E1 but not for binding to DNA structures ("Metal ions bound at the active site of the junction-resolving enzyme T7 endonuclease I", The EMBO Journal, 2002, 21:13, 3505-3515); in one embodiment the T7E1 nuclease will be used to bind mismatch structures in the absence of catalytic metal ions. Therefor removing of depleting all, one or more of these metal ions in the reaction solution for the formation of a protein/mismatch duplex structure will inhibit the catalytic activity of the endonuclease yet permit binding of the endonuclease to the mismatch duplex structure. In an alternative embodiment chelating agents such as ethylenediaminetetraacetic acid (EDTA) can be used to bind metal ions and prevent cleavage of bound DNA structures by the enzyme. Alternatively, as identified by Parkinson et al. ("Catalytic and binding mutants of the junction-resolving enzyme endonuclease I of bacteriophage T7: role of acidic residues", NAR, 1999, 27:2, 682-689), there are five residues: E20, E35, E65, D55, and D74, that are essential to catalytic activity. The replacement of these residues with other amino acids renders the protein catalytically inactive while retaining the ability to selectively bind junctions. Of particular interest is the E65K variant, which exhibits >12× greater affinity than the WT T7E1. ("Binding of the Junction-resolving Enzyme Bacteriophage T7 Endonuclease I to DNA: Separation of Binding and Catalysis by Mutation", J. Mol. Bio., 1995, 246, 95-107) In one embodiment, an engineered T7E1 with an amino acid substitution at one of the catalytically critical positions, E20, E35, E65, D55, or D74, is used to recognize and capture DNA structures associated with mismatches. In a particular embodiment the variant E65K is used to capture structures associated with mismatches.

T4 endonuclease 7 (T4E7) (SEQ ID NO:2): The T4 endonuclease VII is encoded by the bacteriophage T4, and while functionally similar to T7E1, comes from a different superfamily of enzymes. T4E7 is able to bind and cleave four-way junctions as well as Y-junctions, heteroduplex loops, single-strand overhands, curved DNA, and single-base mismatches. ("Conformational flexibility in T4 endonuclease VII revealed by crystallography: implications for substrate binding and cleavage," J. Mol. Biol, 2001, 308, 311-323). T4E7 contains two metal binding domains, the first is a Zn-coordination domain required for binding to DNA ("The modular character of a DNA junction resolving enzyme: a zinc binding motif in T4 endonuclease VII", J. Mol. Biol, 1995, 252, 596-610) and the second coordinates Mg or Mn and is responsible for the nuclease activity of the enzyme. In the absence of Mg and Mn, T4E7 is able to bind but not cleave DNA structures. ("T4 Endonuclease VII, Importance of a histidine-aspartate cluster within the zinc-binding domain", J. Biol. Chem., 1996, 271:51), In one embodiment, the T4E7 nuclease is used to bind mismatch structures in the absence of catalytic metal ions, or, for example, where the reaction solution is depleted of Mg and Mn, but not Zn.

Alternatively, the E86A variant is able to bind but not cleave DNA junctions. ("T4 Endonuclease VII selects and alters the structure of the four-way DNA junction; binding of a resolution-defective mutant enzyme", 1996, 260, 678-696). The D40N, D40A, and H41T variants of T4E7 are inactive while retaining affinity for DNA junctions, making them additional suitable candidates. Of particular interest is the H38S and H43T variants. These enzymes exhibit >7× increased binding affinity over the wild type enzyme. The H43T variant shows low activity while the H38S has thermally-sensitive enzymatic activity. ("T4 Endonuclease VII, Importance of a histidine-aspartate cluster within the zinc-binding domain", J. Biol. Chem., 1996, 271:51). In an alternative embodiment, the H38S or H43T variants are used in the absence of catalytic metal ions to bind mismatch structures. In a further embodiment the H38S variant is used in conjunction with thermal control to modulate catalytic activity of the enzyme and to bind mismatch structures.

CEL II: The celery derived endonucleases CEL I (SEQ ID NO:3) and CEL II (Surveyor™) (SEQ ID NO:4) exhibit highly specific activity towards mismatches in dsDNA. In in vitro cleavage assays, CEL II provides detection of single nucleotide changes that is superior to T7E1. ("Comparison of T7E and Surveyor Mismatch Cleavage Assays to Detect Mutations Triggered by Engineered Nucleases", G3, 2015 Mar. 5, 407-415). The CELI nuclease requires $Zn^{2+}$ and $Mg^{2+}$ for activity at neutral pH. Reduced pH (5.5) and eliminating $Mg^{2+}$ reduce cleavage, though the role of $Mg^+$, may be related to substrate recognition. ("Purification, cloning, and characterization of the CEL I Nuclease", Biochemistry, 2000, 39, 3533-3541) Consequently, in one embodiment CEL I is used at pH 5.5 to capture mismatches. CEL II requires $Mg^{2+}$, $Ca^{2+}$, or $Sr^{2+}$ for activity, while no activity is seen for $Zn^{2+}$, $Cu^{2+}$, $Ni^{2+}$, and $Co^{2+}$. ("Production and characterization of the celery mismatch endonuclease CEL II using baculovirus/silkworm expression system", Appl. Mircobiol. Biotecnol., 2013, 97, 6813-6822). In one embodiment, CELII is used to recognize and capture mismatches in the presence of Zn2+ but without $Mg^{2+}$, $Ca^{2+}$, or $Sr^{2+}$.

MutS: The mismatch repair protein MutS (SEQ ID NO:5) is found in *E. coli* and other prokaryotes. MutS binds to mismatches or short indels, ("Sequence-specific and DNA structure-dependent interactions of *Escherichia* cob MutS and human p53 with DNA", Analytical Biochemistry, 2013, 442) but does not have affinity for homoduplex DNA or 3'-overhang DNA ends (Determination of protein-DNA binding constants and specificities from statistical analyses of single molecules: MutS-DNA interactions. In one embodiment, MutS is used to recognize and capture mismatches and short indels.

MSH2-MSH3/MSH2-MSH6: The mismatch repair proteins MSH2 (SEQ ID NO:6), MSH3 (SEQ ID NO:7), and MSH6 (SEQ ID NO:8) are MutS homologues found in eukaryotes. They form heterodimeric complexes, MSH2-MSH3, which recognizes small loops (1-13 nt) in length, and MSH2-MSH6, which recognizes mismatches and single nucleotide loops, similar to MutS. As shown by Surtees et al., ("Mismatch Repair Factor MSH2-MSH3 Binds and Alters the Conformation of Branched DNA Structures Predicted to form During Genetic Recombination", J. Mol. Bio., 2006, 360, 523-536), MSH2-MSH3 specifically binds at the double-strand/single-strand junction of branched substrates. The affinity to a 8-nt loop or to a frayed end was at least 2× that of ssDNA and 4× that of dsDNA. Consequently, MSH2-MSH3 can be used to identify and capture DNA associated with indels that are larger than 8 nt.

Saw1 (SEQ ID NO:9) is a structure-specific DNA binding protein with a high affinity for frayed ends (splayed-Y) and 3'-flap DNA. As reported by Li et al., ("Role of Saw1 in Rad1/Rad10 complex assembly at recombination intermediates in budding yeast," The EMBO Journal, 2013 Jan. 8, 32:3, 461-472), SAW-1 has a high affinity for splayed arm (frayed end) structures as well as 5'- or 3'-flap DNA, but only a weak affinity for ssDNA and 5' or 3' overhangs and no affinity for heteroduplex DNA. Saw1 will bind to larger bubble structures associated with indels (>14 bp) but does not bind to smaller bubbles (<7 nt). Consequently, Saw1 protein can be used to identify and capture DNA associated with indels that are larger than 14 nt.

XPA, (SEO ID NO:10) Human xeroderma pigmentosa group A is essential to nucleotide excision repair and can bind specifically ds-ssDNA junctions. XPA binds frayed ends, 3'-overhangs, and 5'-overhangs and DNA bubble substrates as small as 6-nts, but shows no affinity towards ssDNA or dsDNA. ("Specific and efficient binding of XPA to double-strand/single strand DNA junctions with 3'- and/or 5'-ssDNA branches", Biochemistry, 2006 Dec. 26, 45:51, 15921-15930) Consequently XPA can be used to bind and capture indels larger than 6-nts.

Genomic fragment enrichment (GFE). In the case of a non-homogeneous population of organisms, an initial enrichment step will be performed to capture the target genetic material. Sample DNA for analysis will first be processed to make large-insert capture libraries. This hybridization capture method is currently exploited for metagenomics purposes across multiple phyla. ("Revealing large metagenomics regions through long DNA fragment hybridization capture", Microbiome, 2017, 5:33) Incubation of the sample DNA with specific genomic capture probes will allow enrichment of large genomic regions of the strain of interest. GFE allows for the capture of sequences of at least tens of kilobases via hybridization with short, non-overlapping probes specific to a particular gene. Genome-wide probe sets will be generated based on multi-sequence alignment and selection of conserved elements.

Data analysis and assessment of probability of engineering. In one embodiment, the method for sequencing and analysis is paired-end NGS, though alternative sequencing techniques such as nanopore sequencing can also be used. To analyze the data reference genome derived by concatenating the sequences of the chassis organisms is generated. Sequences with multiple mismatches with multiple independent UMIs are flagged as sequences with moderate likelihood of being an engineered SNP or codon optimization. 'De novo' assembly, aided by UMIs, regions that do not align to the reference genome is used to differentiate between sequencing artifacts and highly engineered regions. Regions with multiple independent lines of evidence for multiple modifications are considered a moderate likelihood of engineering. If this is combined with a sequence aligning to an organism not in a reference database, the organism will be considered a high-likelihood engineered organism.

Poor DNA quality/quantity. DNA is susceptible to many types of damage resulting from exposure to many chemicals, environmental conditions, and manipulation. The sensitivity and specificity of this method can potentially be influenced by the quality of sample DNA. In one embodiment commercially available enzyme cocktails (i.e. NEB PreCR kit) will be used to repair DNA. The repair mechanisms are not perfect, and thus are not be appropriate for the detection of SNPs, but it is possible to repair genes with enough fidelity they would still hybridize to their capture probe.

An intrinsic problem for many NGS techniques is the preparation of large enough amounts of input DNA. An inherent problem with amplification of DNA by PCR is the introduction of bias, where certain DNA sequences are preferentially amplified. To mitigate for this, in one embodiment, any samples that require amplification are amplified with a high fidelity proof-reading polymerase over fewer amplification cycles, reducing the possibility of perpetuating error.

Example 1: HIP-Seq Workflow

To produce biotinylated capture probes, depicted in FIG. 2-1 as lines with a dark sphere on the end representing the biotin group, first genomic DNA from a reference organism is extracted and purified using standard techniques. For example, for *P. aeruginosa*, genomic DNA was purified from the reference strain PAO using the Epicentre MasterPure kit, according to the manufacturer's instructions. The reference genome DNA can be fragmented into segments of a specified length, ranging from about 100-about 10,000 nucleotides. Fragments are prepared either using commercially available instruments for sonication (eg., Covaris, QSonica, or Diagenode) or using enzymatic approaches (eg. NEBNext® dsDNA Fragmentase®). Following fragmentation, the DNA is size selected and purified by polyacrylamide gel electrophoresis.

A variety of approaches are suitable for biotinylation of the reference probes, including 3' biotinylation using a tailing reaction with the template-independent polymerase terminal deoxynucleotidyl transferase; 5' biotinylation by PCR with biotinylated $NS_5$ oligo (G+C-rich); and internal biotin incorporation by Klenow fragment extension with biotin-14-dCTP and random octamers). In some implementations, an additional size selection step may take place after probe production.

Genomic DNA is extracted from the sample, indicated by the using standard techniques known to those skilled in the art, such as commercially available kits for DNA extraction and purification (eg. NEB Monarch, QIAGEN DNeasy or QIAamp, Epicentre MasterPure. FIG. 2-1, top, shows a representation of an engineered cell. The two lines inside the oval represent the double stranded genomic DNA with a light colored engineered insertion sequence in the dark colored genomic background.

The sample DNA is fragmented either mechanically or enzymatically using methods similar to those described to prepare the capture probes. The sample DNA fragments are mixed with the biotin-labeled capture probes, heated to ~95° C. to eliminate secondary structure and then cooled slowly to allow sample and capture probe DNA to hybridize, as shown in FIG. 2-2. DNA sequences that are not found in the reference genome either are associated with a biotinylated probe and result in mismatch structures such as loops or frayed ends or are not hybridized to any biotinylated probe DNA.

T7E1, or an alternative mismatch recognition protein is mixed with the sample DNA under suitable reaction conditions (e.g., if the protein is an endonuclease, suitable reaction conditions can include reaction in a solution depleted of the metal ions required for catalytic activity of the endonuclease) and allowed to interact for between 1 about 5 min to about 1 hr. The protein binds to mismatch duplex structures, as is shown in FIG. 2-3. The protein is then crosslinked to the DNA by standard techniques such as with formaldehyde or using UV light. Antibodies that recognize the His-affinity tag, an alternative affinity tag on the mismatch recognition protein, or the protein directly are attached to agarose beads and used for immunoprecipitation of the protein-DNA complexes that contain mismatches (FIG. 2-4, bottom) separating the sample into two fractions. In the fraction without mismatches (FIG. 2-5, top), streptavidin-modified magnetic beads are used to remove the reference probe samples, leaving only DNA from the sample that is not found in the reference genome sample (FIG. 2-6, top). In the fraction with mismatches, the probe DNA and sample DNA are dehybridized (e.g. by heat). Magnetic beads are then used to remove the probe DNA (FIG. 2-5, bottom), leaving behind only sample DNA that contains mismatches with the reference genome (FIG. 2-6, bottom).

Standard library prep kits (for example, obtained from Illumina) are used to prepare these DNA fragments for NGS and the DNA is sequenced to identify differences between the sample and reference genome.

Example 2: Protein Expression of T7E1, T4E7, and CELII Containing Affinity Tags

Figure 3B:
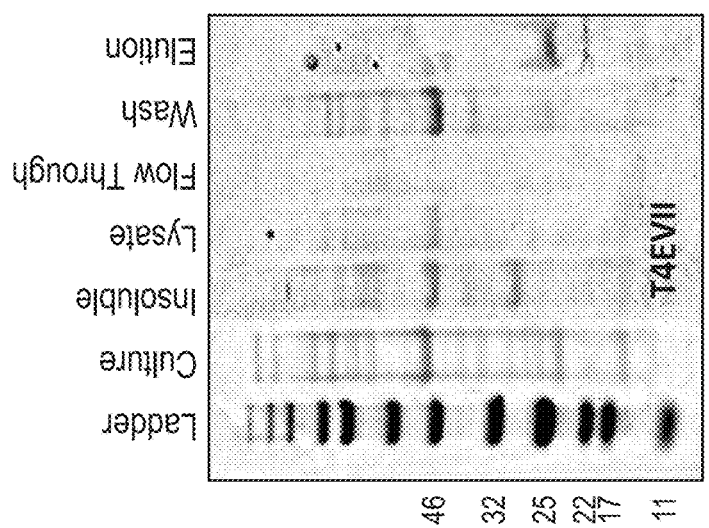
Figure 3A:
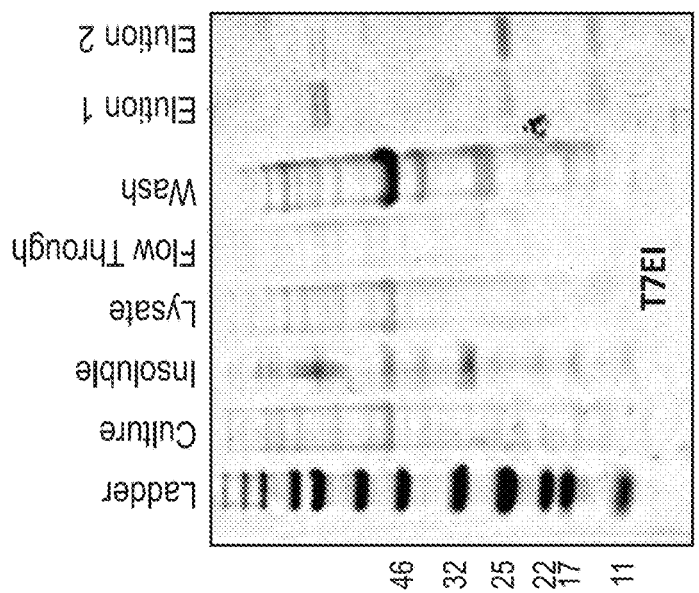

The protein expression vector pET28b was used to introduce an N-terminal His-tag in frame with the coding sequence of three endonucleases, T7E1, T4E7, and CELII. While any common affinity tags may be introduced, of particular note are VSV-G, FLAG, MBP, Twin-Strep, and S-Tag. Plasmids were verified by sequencing, and transformed into the expression strain *E. coli* BL21 (DE3) where expression of the fusion proteins is controlled by an IPTG-inducible promoter. Expression of the enzymes was induced and enzymes were purified using affinity chromatography with a Ni-NTA resin. Coomassie-stained protein gels show successful expression of T7E1 (FIG. 3A), T4E7 (FIG. 3B), and CELII (FIG. 3C) with successful purification of T7E1 (FIG. 3A) and T4E7 (FIG. 3B).

Example 3: Recognition of Mismatch Structures by T7E1 and Surveyor (CELII) Nucleases To test recognition, binding and cleavage of mismatches by mismatch recognition proteins, five test probe sets were designed and synthesized. These probes enable determination of the DNA substrates that are recognized by mismatch recognition proteins and to test multiple conditions and approaches that influence recognition, binding and cleavage of mismatches. Probe set 1 and 4 have perfect matches (FIG. 3-1, 3-4, bottom) between the bait and prey strands; set 2 has frayed ends, a large region of mismatch at one end (FIG. 3-2, bottom); set 3 has a 600 bp perfect match between bait and prey, but a 100-nucleotide overhang at one end; and set 5 has a 3-bp mismatch between the bait and prey in the middle.

Probe sets were prepared by PCR of a dsDNA with different templates using a forward primer oligo with 5'-phosphorothioate bonds and a reverse primer oligo that is 5'-phosphorylated. After PCR purification, lambda exonuclease digestion provided selective digestion of the phosphorylated reverse strand. The ssDNA probe was purified using Ampure beads.

Figure 4:
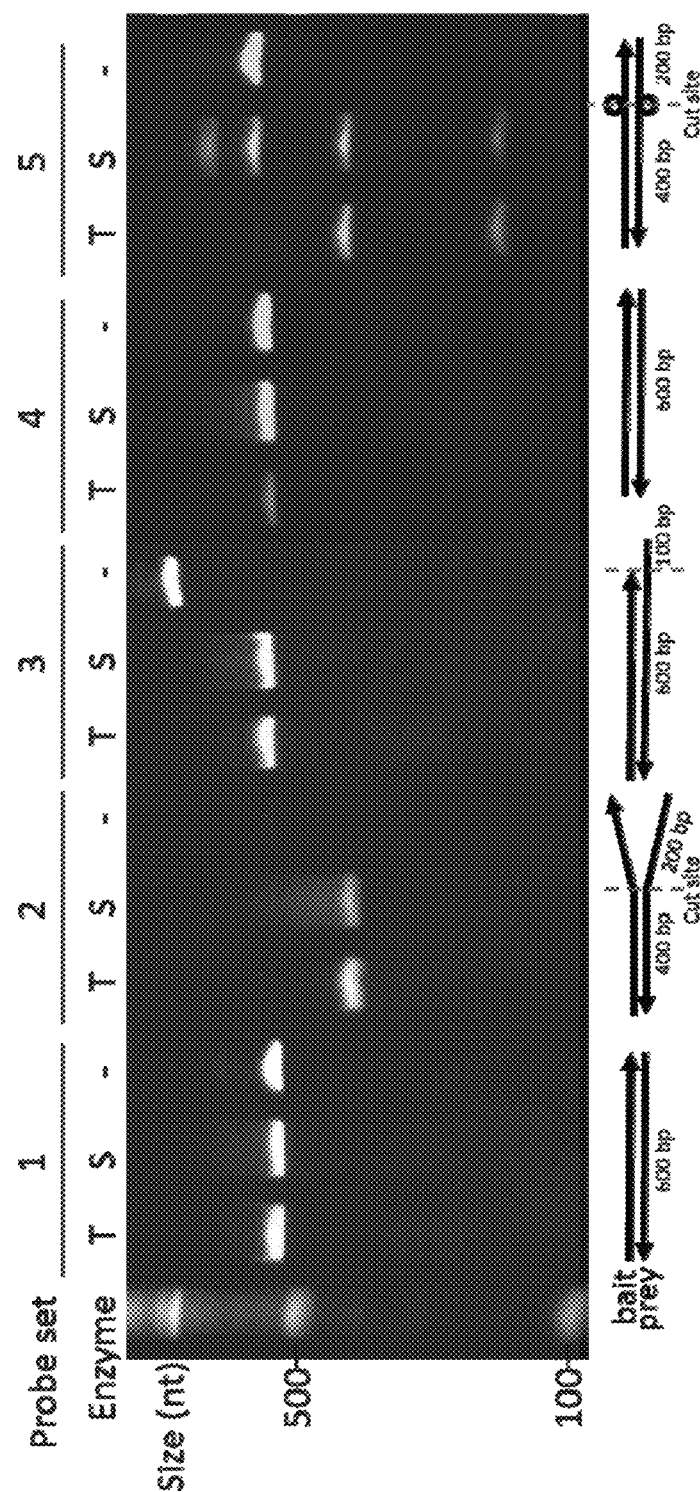
FIG. 4 depicts a denaturing DNA electrophoresis gel with results of a cleavage assay by T7E1 (T) and Surveyor nuclease (S). Five sets of annealed DNA probes were incubated individually with T7E1 or Surveyor nuclease, denatured and separated on 6% TBE-Urea gel, stained with GelRed dye for visualization.

The bait and prey ssDNA strands were hybridized and incubated with either T7E (NEB) or Surveyor nuclease (IDT). FIG. 4 shows a DNA electrophoresis gel (6% TBE-Urea) with the results of this experiment. Both T7E1 and Surveyor cleaved probe sets 2, 3, and 5, and had no effect on probe set 1 and 4 indicating that the nuclease recognizes and cleaves not only mismatches but also overhang structures.

Figure 5:
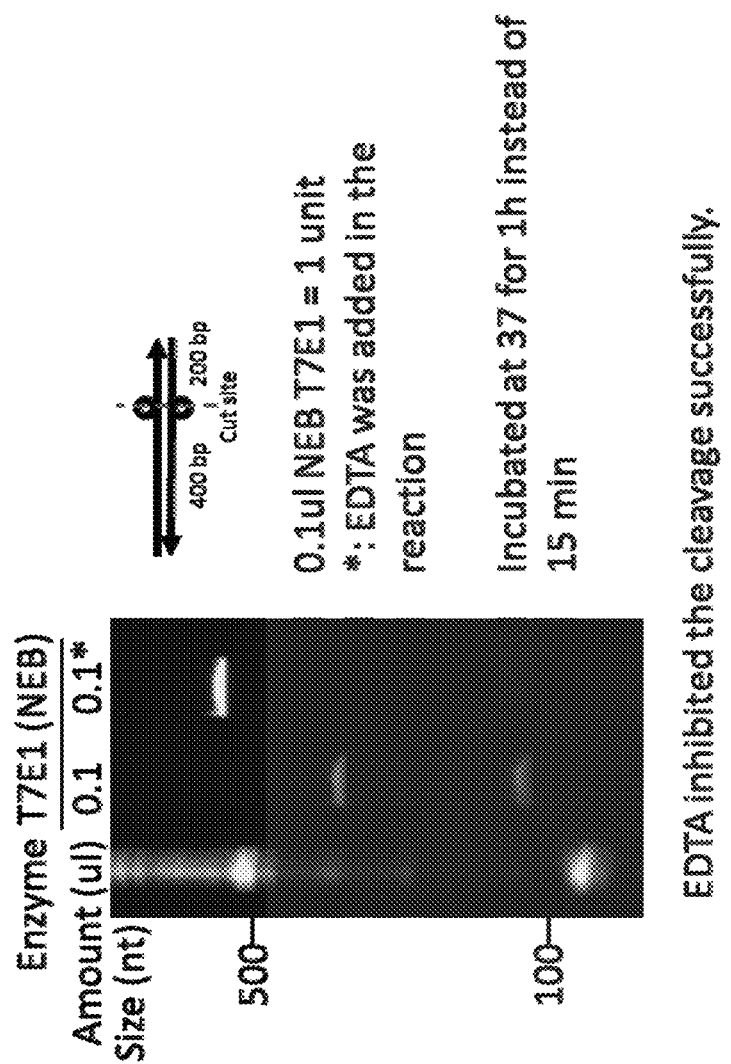
FIG. 5 shows a denaturing DNA electrophoresis assay with results of a cleavage assay by T7E1 as described herein in the presence of the chelating agent, EDTA.

Ideally, mismatched DNA is captured, partitioned, and sequenced without cleavage occurring. The chelating agent, ethylenediaminetetraacetic acid (EDTA) was used to test the impact of metal ions on the activity of T7E1. For this experiment, 1 unit (1 µl) of T7E (NEB), was incubated with probe set 3 (3-bp mismatch) for one hour with and without EDTA. The DNA electrophoresis gel shown in FIG. 5 shows that the addition of EDTA successfully inhibited cleavage by the T7E1 enzyme.

Elimination of 3'- and 5'-overhangs: Enzymes such as T7E1 and T4E7 as well as proteins such as XPA have affinity for DNA structures that are markers of engineering, such as frayed ends, bubbles, and mismatches, however they also have some affinity for 3'- and 5'-overhangs. Because of the randomness of the DNA fragmentation process overhang-containing duplexes will be common, and predominantly not an indication of genetic modification. The two examples below describe strategies for the substantial elimination of, or significant reduction in, overhang-containing duplexes. Suitable enzymes and conditions for these reactions are known to those of skill in the art, or are readily optimized for standard protocols.

Example 4: Elimination of Overhangs Through Circularization

After hybridization between reference and sample DNA, an enzyme such as CircLigase (Lucigen) can be used to circularize one of the DNA strands (see for example, FIG. 6). Next, a DNA polymerase is used to fill in any gaps in the circularized DNA. In the case where there is a 3'- and/or 5'-overhang, the polymerase will fully circularize the second strand creating circularized dsDNA FIG. 6A, top resulting in a gap-free dsDNA circle. In the case of a frayed end, the polymerase will leave a flap behind (FIG. 6B, middle). In the case of a bubble or SNP, the polymerase will create a fully circularized dsDNA, but the bubble will remain (FIG. 6C, bottom). A mismatch recognition protein (MMR) is then able to recognize and capture the structures associated with genetic modifications.

Example 5: Elimination of Overhangs Through the Use of Klenow Fragment and Exonuclease VII Klenow fragment enzyme and exonuclease VII can be used in a reaction, substantially simultaneously, or sequentially, as described herein to eliminate overhang-containing duplex structures. Klenow fragment is a proteolytic product of *E. coli* DNA polymerase. It retains polymerase activity but lacks both 5'-3' and 3'-5' exonuclease activity. Exonuclease VII (ExoVII) is a nuclease that selectively cleaves 3'- and 5'-overhangs. In one embodiment, after hybridization between the reference and sample DNA, Klenow fragment is used to extend the complementary strand of the 5'-overhang to make it blunt, and ExoVII is used to eliminate the 3'-overhangs. Next, the mismatch recognition protein is used to capture structures of interest.

In an alternative embodiment, after hybridization between the reference and sample DNA, the mismatch recognition protein (or cocktail of proteins) is used to capture DNA that has structures of interest as well as overhangs. This enables the partitioning of non-hybridized sample ssDNA sequences. After partitioning, Klenow fragment and ExoVII are introduced sequentially to eliminate 5'- and 3'-overhangs. A second mismatch protein recognition step is used to isolate structures of interest that contain an internal mismatch within the duplex.

REFERENCES CITED IN THE APPLICATION (THE TEACHINGS OF WHICH ARE HEREIN INCORPORATED BY REFERENCE IN THEIR ENTIRETY)

"Comparative genomic hybridization", Annual Review of Genomics and Human Genetics, 2005 Sep. 22, 6, 331-354.

"The use of resolvases T4 Endonuclease VII and T7 Endonuclease I in mutation detection", Mol. Biotech. 2003, 23, 73-81.

"Screening for mutations by enzyme mismatch cleavage with T4 endonuclease VII", PNAS, 1995 January, 92, 87-91.

*Comparison of T7E1 and Surveyor Mismatch Cleavage Assays to Detect Mutations Triggered by Engineered Nucleases". G3*, 2015 Mar. 5, 407-415.

"*Mismatch cleavage by single-strand specific nucleases*". *NAR*, 2004, 32:8, 2632-2641.

"Catalytic and binding mutants of the junction-resolving enzyme endonuclease 1 of bacteriophage T7: the role of acid residues", NAR, 1999, 27:2, 682-689.

"The Active Site of the Junction-resolving Enzyme T7 Endonuclease I", J. Mol. Bio., 2001, 307, 1145-1158.

"Development of a simple and highly sensitive mutation screening system by enzyme mismatch cleavage with optimized conditions for standard laboratories", Electrophoresis, 2008, 29.

"Binding of the Junction-resolving Enzyme Bacteriophage T7 Endonuclease I to DNA: Separation of Binding and Catalysis by Mutation", J. Mol. Bio., 1995, 246, 95-107.

"Conformational flexibility in T4 endonuclease VII revealed by crystallography: implications for substrate binding and cleavage," J. Mol. Biol, 2001, 308, 311-323.

"The modular character of a DNA junction resolving enzyme: a zinc binding motif in T4 endonuclease VII", J. Mol. Biol, 1995, 252, 596-610.

"T4 Endonuclease VII selects and alters the structure of the four-way DNA junction; binding of a resolution-defective mutant enzyme", J. Mol. Biol. 1996, 260, 678-696.

"*Purification, cloning, and characterization of the CEL I Nuclease*". Biochemistry. 2000, 39, 3533-3541.

*Production and characterization of the celery mismatch endonuclease CEL II using baulovirus/silkworm expression system*". Appl. Mircobiol. Biotecnol., 2013, 97, 6813-6822.

"Mismatch Repair Factor MSH2-MSH3 Binds and Alters the Conformation of Branched DNA Structures Predicted to form During Genetic Recombination", J. Mol. Bio., 2006, 360, 523-536.

"Role of Saw1 in Rad1/Rad10 complex assembly at recombination intermediates in budding yeast," The EMBO Journal, 2013 Jan. 8, 32:3, 461-472.

"Specific and efficient binding of XPA to double-strand/single strand DNA junctions with 3'- and/or 5'-ssDNA branches", Biochemistry, 2006 Dec. 26, 45:51, 15921-15930.

"Revealing large metagenomics regions through long DNA fragment hybridization capture", Microbiome, 2017, 5:33.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying one, or more, genetic modifications in an organism, the method comprising;
   a.) obtaining a sample from the organism, wherein the sample comprises DNA;
   b.) hybridizing the DNA in the sample with labelled nucleic acid probes complementary to cognate organism DNA under conditions suitable for the formation of a hybridization mixture comprising probe/sample DNA match duplex structures and/or mismatch duplex structures;
   c.) contacting the mixture of hybridized probe/sample DNA comprising the match and mismatch duplex structures of step b.) with one, or more mismatch recognition proteins comprising a genetically-engineered, non-catalytic endonuclease capable of specifically interacting with the mismatch duplex structures of the mixture under conditions suitable for the formation of a protein/mismatch duplex structure complex;
   d.) recovering the protein/mismatch duplex structure complexes of step c.);
   e.) releasing the mismatch duplex structure DNA from the protein; and
   f.) sequencing the released DNA to determine if a genetic modification is present in the sample DNA that is not present in the cognate organism DNA.

2. The method of claim 1, wherein the genetic modification is an insertion, a deletion or a single nucleotide polymorphism in the genome of the organism.

3. The method of claim 1, wherein the organism is a prokaryotic or a eukaryotic organism or a virus.

4. The method of claim 3, wherein the eukaryotic organism is a yeast, fungi, protozoa, algae, plant or mammal.

5. The method of claim 4, wherein the mammal is a human.

6. The method of claim 4, wherein the sample from the plant or mammal comprises cells containing DNA.

7. The sample of claim 6, wherein the sample comprises blood cells, epithelial cells, saliva, feces, cerebral spinal fluid, sweat or tears.

8. The method of claim 1, wherein the endonuclease is a variant of endonuclease T7E, T4E7, CEL I or CEL II.

9. The variant endonuclease of claim 8, wherein the endonuclease is T7E1 comprising SEQ ID NO: 1 with a mutation located at one or more residues: E20, E35, D55, E65 or D74.

10. The variant endonuclease of claim 9, wherein the endonuclease is T7E1 comprising SEQ ID NO: 1 with a E65K mutation.

11. The variant endonuclease of claim 8, wherein the endonuclease is T7E4 comprising SEQ ID NO: 2 with a E86A, D40N, D40A, or H41T mutation.

12. The method of claim 10, wherein the endonuclease is T7E1 or and the solution for the formation of a protein/mismatch duplex structure complex is depleted of Mg, Mn, and Zn.

13. The method of claim 10, wherein the endonuclease is T7E1 and a chelating agent such as EDTA is used to bind catalytic metal ions.

14. The method of claim 10, wherein the endonuclease is T4E7 and the solution for the formation of a protein/mismatch duplex structure complex is depleted of Mg and Mn but not Zn.

15. The method of claim 14, wherein the endonuclease is T4E7 comprising SEQ ID NO: 2 with a H38S or H43T mutation.

16. The method of claim 10, wherein the endonuclease is CEL II and the solution for the formation of a protein/mismatch duplex structure complex is depleted of Mg, Ca, and Sr, but not Zn.

17. The method of claim 1, wherein the method additionally comprises one, or more, steps to eliminate overhang-containing duplex structures formed in step b.).

18. The method of claim 17, wherein the elimination steps comprise:
   i.) circularizing one of the DNA strands of overhang-containing duplex structures formed in step b.); and
   ii.) contacting the circularized DNA strand with a DNA polymerase, under conditions suitable for addition of nucleotides, resulting in gap-free circularized dsDNA.

19. The method of claim 17, wherein the overhang elimination step comprises contacting the overhang-containing duplex structures formed in step b.) substantially simultaneously, or sequentially with Klenow fragment and ExoVII under conditions suitable for eliminating overhang-containing duplex structures.

20. The method of claim 17, wherein the elimination steps comprise:
   i.) contacting protein/mismatch duplex structures formed in step c.) with Klenow fragment under conditions suitable for the extension of the complementary strand of 5' overhangs;

ii.) substantially simultaneously, or sequentially contacting the protein/mismatch duplex structures formed in part c.) with ExoVII under conditions suitable for the cleavage of 3' overhangs; and iii.) repeating step c.) of claim 1.

21. A method of detecting one, or more genetic modifications in a sample comprising DNA obtained from an organism of interest, the method comprising:
   a.) contacting the sample with specific genomic capture probes under suitable conditions for the capture probes to hybridize with target DNA in the sample, thereby enriching the target DNA in the sample;
   b.) fragmenting the enriched target DNA;
   c.) contacting the fragmented target DNA with labelled, cognate probes generated from the reference genome of the organism of interest under conditions suitable for the formation of a hybridization mixture comprising target DNA/probe duplexes, wherein the duplexes comprise match duplex structures and/or mismatch duplex structures;
   d.) contacting the mixture of step c.) with one, or more affinity-tagged mismatch recognition proteins comprising a genetically-engineered, non-catalytic endonuclease capable of specifically interacting with the mismatch duplex structures of the mixture under conditions suitable for the formation of a protein/mismatch duplex structure complex;
   e.) contacting the protein/mismatch duplex structure complexes of step d.) with an antibody, or antibody fragment, that specifically binds to the affinity tag of the protein, thereby immunoprecipitating the protein/mismatch duplex complexes of step d.);
   f.) separating the mismatch duplex structure from the antibody-bound protein to obtain labelled mismatch duplex structures;
   g.) denaturing the labelled mismatch duplex structures to obtain mismatch target DNA; and
   h.) sequencing the mismatch target DNA to detect the presence or absence of a genetic modification.

22. The method of claim 21, wherein the genetic modification is an insertion, a deletion or a single nucleotide polymorphism.

23. The method of claim 21, wherein the organism is a prokaryotic or a eukaryotic organism or a virus.

24. The method of claim 23, wherein the eukaryotic organism is a yeast, fungi, protozoa, algae, plant or mammal.

25. The method of claim 24, wherein the mammal is a human.

26. The method of claim 24, wherein the sample from the plant or mammal comprises cells containing DNA.

27. The sample of claim 26, wherein the sample comprises blood cells, epithelial cells, saliva, feces, cerebral spinal fluid, sweat or tears.

28. The method of claim 21, wherein the endonuclease is a variant of endonuclease T7E, T4E7, CEL I or CEL II.

29. The variant endonuclease of claim 28, wherein the endonuclease is T7E1 comprising SEQ ID NO: 1 with a mutation located at one or more residues: E20, E35, D55, E 65 or D74.

30. The variant endonuclease of claim 29, wherein the endonuclease is T7E1 comprising SEQ ID NO: 1 with a E65K mutation.

31. The variant endonuclease of claim 28, wherein the endonuclease is T4E7 comprising SEQ ID NO:2 with a mutation located at one, or more residues: D40N, D40A, H38S, H41T and H43T.

32. The method of claim 21, wherein prior to step e.), the protein/heteroduplex DNA complexes are cross-linked.

33. The method of claim 21, wherein prior to sequencing in step h.) the sample is amplified.

34. The method of claim 21, further comprising:
   i.) recovering the supernatant from the immunoprecipitation step e.) wherein the supernatant comprises labelled match duplex structures and unhybridized DNA;
   j.) contacting the supernatant with streptavidin coated magnetic beads under conditions suitable for the labelled match duplex structures to bind to the beads;
   k.) recovering the unhybridized DNA from step j.);
   l.) optionally amplifying the DNA; and
   m.) sequencing the unhybridized DNA.

35. The method of claim 21, wherein the method additionally comprises one, or more, steps to eliminate overhang-containing duplex structures formed in step c.).

36. The method of claim 35, wherein the elimination steps comprise:
   i.) circularizing one of the DNA strands of overhang-containing duplex structures formed in step c.); and
   ii.) contacting the circularized DNA strand with a DNA polymerase, under conditions suitable for addition of nucleotides, resulting in gap-free circularized dsDNA.

37. The method of claim 35, wherein the overhang elimination step comprises contacting the overhang-containing duplex structures formed in step c.) substantially simultaneously, or sequentially with Klenow fragment and Exo VII under conditions suitable for eliminating overhang-containing duplex structures.

38. The method of claim 35, wherein the elimination steps comprise:
   i.) contacting protein/mismatch duplex structures formed in step d.) with Klenow fragment under conditions suitable for the extension of the complementary strand of 5' overhangs;
   ii.) substantially simultaneously, or sequentially contacting the protein/mismatch duplex structures formed in part c.) with ExoVII under conditions suitable for the cleavage of 3' overhangs; and
   iii.) repeating step d.) of claim 21.

39. The method of claim 1, wherein prior to step b.) the DNA in the sample is enriched for target DNA in the sample by contacting the sample with specific genomic capture probes under suitable conditions for the capture probes to hybridize with target DNA in the sample, thereby enriching the target DNA in the sample, and fragmenting the enriched target DNA.

* * * * *

SEQUENCE LISTING

<160> NUMBER OF SEQ ID NOS: 10

<210> SEQ ID NO 1
<211> LENGTH: 149
<212> TYPE: PRT
<213> ORGANISM: Enterobacteria phage T7

<400> SEQUENCE: 1

Met Ala Gly Tyr Gly Ala Lys Gly Ile Arg Lys Val Gly Ala Phe Arg
1               5                   10                  15

Ser Gly Leu Glu Asp Lys Val Ser Lys Gln Leu Glu Ser Lys Gly Ile
            20                  25                  30

Lys Phe Glu Tyr Glu Glu Trp Lys Val Pro Tyr Val Ile Pro Ala Ser
        35                  40                  45

Asn His Thr Tyr Thr Pro Asp Phe Leu Leu Pro Asn Gly Ile Phe Val
    50                  55                  60

Glu Thr Lys Gly Leu Trp Glu Ser Asp Asp Arg Lys Lys His Leu Leu
65                  70                  75                  80

Ile Arg Glu Gln His Pro Glu Leu Asp Ile Arg Ile Val Phe Ser Ser
                85                  90                  95

Ser Arg Thr Lys Leu Tyr Lys Gly Ser Pro Thr Ser Tyr Gly Glu Phe
            100                 105                 110

Cys Glu Lys His Gly Ile Lys Phe Ala Asp Lys Leu Ile Pro Ala Glu
        115                 120                 125

Trp Ile Lys Glu Pro Lys Lys Glu Val Pro Phe Asp Arg Leu Lys Arg
    130                 135                 140

Lys Gly Gly Lys Lys
145

<210> SEQ ID NO 2
<211> LENGTH: 157
<212> TYPE: PRT
<213> ORGANISM: Unknown
<220> FEATURE:
<221> NAME/KEY: source
<223> OTHER INFORMATION: /note="Description of Unknown:
      Bacteria recombination endonuclease VII sequence"

<400> SEQUENCE: 2

Met Leu Leu Thr Gly Lys Leu Tyr Lys Glu Glu Lys Gln Lys Phe Tyr
1               5                   10                  15

Asp Ala Gln Asn Gly Lys Cys Leu Ile Cys Gln Arg Glu Leu Asn Pro
            20                  25                  30

Asp Val Gln Ala Asn His Leu Asp His Asp His Glu Leu Asn Gly Pro
        35                  40                  45

Lys Ala Gly Lys Val Arg Gly Leu Leu Cys Asn Leu Cys Asn Ala Ala
    50                  55                  60

Glu Gly Gln Met Lys His Lys Phe Asn Arg Ser Gly Leu Lys Gly Gln
65                  70                  75                  80

Gly Val Asp Tyr Leu Glu Trp Leu Glu Asn Leu Leu Thr Tyr Leu Lys
                85                  90                  95

Ser Asp Tyr Thr Gln Asn Asn Ile His Pro Asn Phe Val Gly Asp Lys
            100                 105                 110

Ser Lys Glu Phe Ser Arg Leu Gly Lys Glu Glu Met Met Ala Glu Met
        115                 120                 125

Leu Gln Arg Gly Phe Glu Tyr Asn Glu Ser Asp Thr Lys Thr Gln Leu
    130                 135                 140

```
Ile Ala Ser Phe Lys Lys Gln Leu Arg Lys Ser Leu Lys
145                 150                 155
```

<210> SEQ ID NO 3
<211> LENGTH: 296
<212> TYPE: PRT
<213> ORGANISM: Apium graveolens

<400> SEQUENCE: 3

```
Met Thr Arg Leu Tyr Ser Val Phe Phe Leu Leu Ala Leu Val Val
1               5                   10                  15

Glu Pro Gly Val Arg Ala Trp Ser Lys Glu Gly His Val Met Thr Cys
            20                  25                  30

Gln Ile Ala Gln Asp Leu Leu Glu Pro Glu Ala Ala His Ala Val Lys
        35                  40                  45

Met Leu Leu Pro Asp Tyr Ala Asn Gly Asn Leu Ser Ser Leu Cys Val
50                  55                  60

Trp Pro Asp Gln Ile Arg His Trp Tyr Lys Tyr Arg Trp Thr Ser Ser
65                  70                  75                  80

Leu His Phe Ile Asp Thr Pro Asp Gln Ala Cys Ser Phe Asp Tyr Gln
                85                  90                  95

Arg Asp Cys His Asp Pro His Gly Gly Lys Asp Met Cys Val Ala Gly
            100                 105                 110

Ala Ile Gln Asn Phe Thr Ser Gln Leu Gly His Phe Arg His Gly Thr
        115                 120                 125

Ser Asp Arg Arg Tyr Asn Met Thr Glu Ala Leu Leu Phe Leu Ser His
    130                 135                 140

Phe Met Gly Asp Ile His Gln Pro Met His Val Gly Phe Thr Ser Asp
145                 150                 155                 160

Met Gly Gly Asn Ser Ile Asp Leu Arg Trp Phe Arg His Lys Ser Asn
                165                 170                 175

Leu His His Val Trp Asp Arg Glu Ile Ile Leu Thr Ala Ala Ala Asp
            180                 185                 190

Tyr His Gly Lys Asp Met His Ser Leu Leu Gln Asp Ile Gln Arg Asn
        195                 200                 205

Phe Thr Glu Gly Ser Trp Leu Gln Asp Val Glu Ser Trp Lys Glu Cys
    210                 215                 220

Asp Asp Ile Ser Thr Cys Ala Asn Lys Tyr Ala Lys Glu Ser Ile Lys
225                 230                 235                 240

Leu Ala Cys Asn Trp Gly Tyr Lys Asp Val Glu Ser Gly Glu Thr Leu
                245                 250                 255

Ser Asp Lys Tyr Phe Asn Thr Arg Met Pro Ile Val Met Lys Arg Ile
            260                 265                 270

Ala Gln Gly Gly Ile Arg Leu Ser Met Ile Leu Asn Arg Val Leu Gly
        275                 280                 285

Ser Ser Ala Asp His Ser Leu Ala
    290                 295
```

<210> SEQ ID NO 4
<211> LENGTH: 310
<212> TYPE: PRT
<213> ORGANISM: Apium graveolens

<400> SEQUENCE: 4

```
Met Gly Met Leu Thr Tyr Thr Gly Ile Tyr Phe Leu Leu Leu Pro
1               5                   10                  15
```

```
Ser Val Phe Cys Trp Gly Lys Gln Gly His Phe Ala Ile Cys Lys Ile
            20                  25                  30

Ala Gln Gly Phe Leu Ser Lys Asp Ala Leu Thr Ala Val Lys Ala Leu
            35                  40                  45

Leu Pro Glu Tyr Ala Asp Gly Asp Leu Ala Ala Val Cys Ser Trp Ala
50                  55                  60

Asp Glu Val Arg Phe His Met Arg Trp Ser Ser Pro Leu His Tyr Val
65                  70                  75                  80

Asp Thr Pro Asp Phe Arg Cys Asn Tyr Lys Tyr Cys Arg Asp Cys His
                85                  90                  95

Asp Ser Val Gly Arg Lys Asp Arg Cys Val Thr Gly Ala Ile His Asn
            100                 105                 110

Tyr Thr Glu Gln Leu Leu Gly Val His Asp Leu Asn Ser Lys Met
            115                 120                 125

Asn Asn Asn Leu Thr Glu Ala Leu Met Phe Leu Ser His Phe Val Gly
            130                 135                 140

Asp Val His Gln Pro Leu His Val Gly Phe Leu Gly Asp Glu Gly Gly
145                 150                 155                 160

Asn Thr Ile Thr Val Arg Trp Tyr Arg Arg Lys Thr Asn Leu His His
                165                 170                 175

Val Trp Asp Thr Met Met Ile Glu Ser Ser Leu Lys Thr Phe Tyr Asn
                180                 185                 190

Ser Asp Leu Ser Ser Leu Ile Gln Ala Ile Gln Ser Asn Ile Thr Gly
            195                 200                 205

Val Trp Leu Thr Asp Ser Leu Ser Trp Ser Asn Cys Thr Ala Asp His
            210                 215                 220

Val Val Cys Pro Asp Pro Tyr Ala Ser Glu Ser Ile Glu Leu Ala Cys
225                 230                 235                 240

Lys Phe Ala Tyr Arg Asn Ala Thr Pro Gly Thr Thr Leu Gly Asp Glu
                245                 250                 255

Tyr Phe Leu Ser Arg Leu Pro Val Ala Glu Lys Arg Leu Ala Gln Ala
            260                 265                 270

Gly Val Arg Leu Ala Ala Thr Leu Asn Arg Ile Phe Thr Ser Asn Pro
            275                 280                 285

Ser Asp Leu Thr Arg Leu Asn Met His Asn Gly Gly His Arg Ser Ser
            290                 295                 300

Asn Asn Ile Glu Ile Val
305                 310

<210> SEQ ID NO 5
<211> LENGTH: 853
<212> TYPE: PRT
<213> ORGANISM: Unknown
<220> FEATURE:
<221> NAME/KEY: source
<223> OTHER INFORMATION: /note="Description of Unknown:
      Proteobacteria DNA mismatch repair protein MutS sequence"

<400> SEQUENCE: 5

Met Ser Ala Ile Glu Asn Phe Asp Ala His Thr Pro Met Met Gln Gln
1               5                   10                  15

Tyr Leu Arg Leu Lys Ala Gln His Pro Glu Ile Leu Leu Phe Tyr Arg
            20                  25                  30

Met Gly Asp Phe Tyr Glu Leu Phe Tyr Asp Asp Ala Lys Arg Ala Ser
            35                  40                  45

Gln Leu Leu Asp Ile Ser Leu Thr Lys Arg Gly Ala Ser Ala Gly Glu
```

-continued

```
                50                  55                  60
Pro Ile Pro Met Ala Gly Ile Pro Tyr His Ala Val Glu Asn Tyr Leu
 65                  70                  75                  80

Ala Lys Leu Val Asn Gln Gly Glu Ser Val Ala Ile Cys Glu Gln Ile
                     85                  90                  95

Gly Asp Pro Ala Thr Ser Lys Gly Pro Val Glu Arg Lys Val Val Arg
                    100                 105                 110

Ile Val Thr Pro Gly Thr Ile Ser Asp Glu Ala Leu Leu Gln Glu Arg
                    115                 120                 125

Gln Asp Asn Leu Leu Ala Ala Ile Trp Gln Asp Ser Lys Gly Phe Gly
                130                 135                 140

Tyr Ala Thr Leu Asp Ile Ser Ser Gly Arg Phe Arg Leu Ser Glu Pro
145                 150                 155                 160

Ala Asp Arg Glu Thr Met Ala Ala Glu Leu Gln Arg Thr Asn Pro Ala
                    165                 170                 175

Glu Leu Leu Tyr Ala Glu Asp Phe Ala Glu Met Ser Leu Ile Glu Gly
                    180                 185                 190

Arg Arg Gly Leu Arg Arg Pro Leu Trp Glu Phe Glu Ile Asp Thr
                    195                 200                 205

Ala Arg Gln Gln Leu Asn Leu Gln Phe Gly Thr Arg Asp Leu Val Gly
                    210                 215                 220

Phe Gly Val Glu Asn Ala Pro Arg Gly Leu Cys Ala Ala Gly Cys Leu
225                 230                 235                 240

Leu Gln Tyr Ala Lys Asp Thr Gln Arg Thr Thr Leu Pro His Ile Arg
                    245                 250                 255

Ser Ile Thr Met Glu Arg Glu Gln Asp Ser Ile Ile Met Asp Ala Ala
                    260                 265                 270

Thr Arg Arg Asn Leu Glu Ile Thr Gln Asn Leu Ala Gly Gly Ala Glu
                    275                 280                 285

Asn Thr Leu Ala Ser Val Leu Asp Cys Thr Val Thr Pro Met Gly Ser
                    290                 295                 300

Arg Met Leu Lys Arg Trp Leu His Met Pro Val Arg Asp Thr Arg Val
305                 310                 315                 320

Leu Leu Glu Arg Gln Gln Thr Ile Gly Ala Leu Gln Asp Phe Thr Ala
                    325                 330                 335

Gly Leu Gln Pro Val Leu Arg Gln Val Gly Asp Leu Glu Arg Ile Leu
                    340                 345                 350

Ala Arg Leu Ala Leu Arg Thr Ala Arg Pro Arg Asp Leu Ala Arg Met
                    355                 360                 365

Arg His Ala Phe Gln Gln Leu Pro Glu Leu Arg Ala Gln Leu Glu Thr
                370                 375                 380

Val Asp Ser Ala Pro Val Gln Ala Leu Arg Glu Lys Met Gly Glu Phe
385                 390                 395                 400

Ala Glu Leu Arg Asp Leu Leu Glu Arg Ala Ile Ile Asp Thr Pro Pro
                    405                 410                 415

Val Leu Val Arg Asp Gly Gly Val Ile Ala Ser Gly Tyr Asn Glu Glu
                    420                 425                 430

Leu Asp Glu Trp Arg Ala Leu Ala Asp Gly Ala Thr Asp Tyr Leu Glu
                435                 440                 445

Arg Leu Glu Val Arg Glu Arg Glu Arg Thr Gly Leu Asp Thr Leu Lys
                450                 455                 460

Val Gly Phe Asn Ala Val His Gly Tyr Tyr Ile Gln Ile Ser Arg Gly
465                 470                 475                 480
```

```
Gln Ser His Leu Ala Pro Ile Asn Tyr Met Arg Arg Gln Thr Leu Lys
            485                 490                 495

Asn Ala Glu Arg Tyr Ile Ile Pro Glu Leu Lys Glu Tyr Glu Asp Lys
            500                 505                 510

Val Leu Thr Ser Lys Gly Lys Ala Leu Ala Leu Glu Lys Gln Leu Tyr
            515                 520                 525

Glu Glu Leu Phe Asp Leu Leu Leu Pro His Leu Glu Ala Leu Gln Gln
        530                 535                 540

Ser Ala Ser Ala Leu Ala Glu Leu Asp Val Leu Val Asn Leu Ala Glu
545                 550                 555                 560

Arg Ala Tyr Thr Leu Asn Tyr Thr Cys Pro Thr Phe Ile Asp Lys Pro
                565                 570                 575

Gly Ile Arg Ile Thr Glu Gly Arg His Pro Val Val Glu Gln Val Leu
            580                 585                 590

Asn Glu Pro Phe Ile Ala Asn Pro Leu Asn Leu Ser Pro Gln Arg Arg
        595                 600                 605

Met Leu Ile Ile Thr Gly Pro Asn Met Gly Gly Lys Ser Thr Tyr Met
        610                 615                 620

Arg Gln Thr Ala Leu Ile Ala Leu Met Ala Tyr Ile Gly Ser Tyr Val
625                 630                 635                 640

Pro Ala Gln Lys Val Glu Ile Gly Pro Ile Asp Arg Ile Phe Thr Arg
                645                 650                 655

Val Gly Ala Ala Asp Asp Leu Ala Ser Gly Arg Ser Thr Phe Met Val
            660                 665                 670

Glu Met Thr Glu Thr Ala Asn Ile Leu His Asn Ala Thr Glu Tyr Ser
        675                 680                 685

Leu Val Leu Met Asp Glu Ile Gly Arg Gly Thr Ser Thr Tyr Asp Gly
        690                 695                 700

Leu Ser Leu Ala Trp Ala Cys Ala Glu Asn Leu Ala Asn Lys Ile Lys
705                 710                 715                 720

Ala Leu Thr Leu Phe Ala Thr His Tyr Phe Glu Leu Thr Gln Leu Pro
                725                 730                 735

Glu Lys Met Glu Gly Val Ala Asn Val His Leu Asp Ala Leu Glu His
            740                 745                 750

Gly Asp Thr Ile Ala Phe Met His Ser Val Gln Asp Gly Ala Ala Ser
        755                 760                 765

Lys Ser Tyr Gly Leu Ala Val Ala Ala Leu Ala Gly Val Pro Lys Glu
        770                 775                 780

Val Ile Lys Arg Ala Arg Gln Lys Leu Arg Glu Leu Glu Ser Ile Ser
785                 790                 795                 800

Pro Asn Ala Ala Ala Thr Gln Val Asp Gly Thr Gln Met Ser Leu Leu
                805                 810                 815

Ser Val Pro Glu Glu Thr Ser Pro Ala Val Glu Ala Leu Glu Asn Leu
            820                 825                 830

Asp Pro Asp Ser Leu Thr Pro Arg Gln Ala Leu Glu Trp Ile Tyr Arg
        835                 840                 845

Leu Lys Ser Leu Val
    850

<210> SEQ ID NO 6
<211> LENGTH: 964
<212> TYPE: PRT
<213> ORGANISM: Saccharomyces cerevisiae S288C
```

<400> SEQUENCE: 6

```
Met Ser Ser Thr Arg Pro Glu Leu Lys Phe Ser Asp Val Ser Glu
1               5                   10                  15

Arg Asn Phe Tyr Lys Lys Tyr Thr Gly Leu Pro Lys Pro Leu Lys
            20                  25                  30

Thr Ile Arg Leu Val Asp Lys Gly Asp Tyr Tyr Thr Val Ile Gly Ser
        35                  40                  45

Asp Ala Ile Phe Val Ala Asp Ser Val Tyr His Thr Gln Ser Val Leu
    50                  55                  60

Lys Asn Cys Gln Leu Asp Pro Val Thr Ala Lys Asn Phe His Glu Pro
65                  70                  75                  80

Thr Lys Tyr Val Thr Val Ser Leu Gln Val Leu Ala Thr Leu Leu Lys
                85                  90                  95

Leu Cys Leu Leu Asp Leu Gly Tyr Lys Val Glu Ile Tyr Asp Lys Gly
                100                 105                 110

Trp Lys Leu Ile Lys Ser Ala Ser Pro Gly Asn Ile Glu Gln Val Asn
            115                 120                 125

Glu Leu Met Asn Met Asn Ile Asp Ser Ser Ile Ile Ala Ser Leu
    130                 135                 140

Lys Val Gln Trp Asn Ser Gln Asp Gly Asn Cys Ile Ile Gly Val Ala
145                 150                 155                 160

Phe Ile Asp Thr Thr Ala Tyr Lys Val Gly Met Leu Asp Ile Val Asp
                165                 170                 175

Asn Glu Val Tyr Ser Asn Leu Glu Ser Phe Leu Ile Gln Leu Gly Val
            180                 185                 190

Lys Glu Cys Leu Val Gln Asp Leu Thr Ser Asn Ser Asn Ser Asn Ala
    195                 200                 205

Glu Met Gln Lys Val Ile Asn Val Ile Asp Arg Cys Gly Cys Val Val
    210                 215                 220

Thr Leu Leu Lys Asn Ser Glu Phe Ser Glu Lys Asp Val Glu Leu Asp
225                 230                 235                 240

Leu Thr Lys Leu Leu Gly Asp Asp Leu Ala Leu Ser Leu Pro Gln Lys
                245                 250                 255

Tyr Ser Lys Leu Ser Met Gly Ala Cys Asn Ala Leu Ile Gly Tyr Leu
                260                 265                 270

Gln Leu Leu Ser Glu Gln Asp Gln Val Gly Lys Tyr Glu Leu Val Glu
            275                 280                 285

His Lys Leu Lys Glu Phe Met Lys Leu Asp Ala Ser Ala Ile Lys Ala
    290                 295                 300

Leu Asn Leu Phe Pro Gln Gly Pro Gln Asn Pro Phe Gly Ser Asn Asn
305                 310                 315                 320

Leu Ala Val Ser Gly Phe Thr Ser Ala Gly Asn Ser Gly Lys Val Thr
                325                 330                 335

Ser Leu Phe Gln Leu Leu Asn His Cys Lys Thr Asn Ala Gly Val Arg
            340                 345                 350

Leu Leu Asn Glu Trp Leu Lys Gln Pro Leu Thr Asn Ile Asp Glu Ile
        355                 360                 365

Asn Lys Arg His Asp Leu Val Asp Tyr Leu Ile Asp Gln Ile Glu Leu
    370                 375                 380

Arg Gln Met Leu Thr Ser Glu Tyr Leu Pro Met Ile Pro Asp Ile Arg
385                 390                 395                 400

Arg Leu Thr Lys Lys Leu Asn Lys Arg Gly Asn Leu Glu Asp Val Leu
                405                 410                 415
```

```
Lys Ile Tyr Gln Phe Ser Lys Arg Ile Pro Glu Ile Val Gln Val Phe
            420                 425                 430

Thr Ser Phe Leu Glu Asp Asp Ser Pro Thr Glu Pro Val Asn Glu Leu
            435                 440                 445

Val Arg Ser Val Trp Leu Ala Pro Leu Ser His His Val Glu Pro Leu
450                 455                 460

Ser Lys Phe Glu Glu Met Val Glu Thr Thr Val Asp Leu Asp Ala Tyr
465                 470                 475                 480

Glu Glu Asn Asn Glu Phe Met Ile Lys Val Glu Phe Asn Glu Glu Leu
            485                 490                 495

Gly Lys Ile Arg Ser Lys Leu Asp Thr Leu Arg Asp Glu Ile His Ser
            500                 505                 510

Ile His Leu Asp Ser Ala Glu Asp Leu Gly Phe Asp Pro Asp Lys Lys
        515                 520                 525

Leu Lys Leu Glu Asn His His Leu His Gly Trp Cys Met Arg Leu Thr
        530                 535                 540

Arg Asn Asp Ala Lys Glu Leu Arg Lys His Lys Lys Tyr Ile Glu Leu
545                 550                 555                 560

Ser Thr Val Lys Ala Gly Ile Phe Phe Ser Thr Lys Gln Leu Lys Ser
                565                 570                 575

Ile Ala Asn Glu Thr Asn Ile Leu Gln Lys Glu Tyr Asp Lys Gln Gln
            580                 585                 590

Ser Ala Leu Val Arg Glu Ile Ile Asn Ile Thr Leu Thr Tyr Thr Pro
        595                 600                 605

Val Phe Glu Lys Leu Ser Leu Val Leu Ala His Leu Asp Val Ile Ala
        610                 615                 620

Ser Phe Ala His Thr Ser Ser Tyr Ala Pro Ile Pro Tyr Ile Arg Pro
625                 630                 635                 640

Lys Leu His Pro Met Asp Ser Glu Arg Arg Thr His Leu Ile Ser Ser
                645                 650                 655

Arg His Pro Val Leu Glu Met Gln Asp Asp Ile Ser Phe Ile Ser Asn
            660                 665                 670

Asp Val Thr Leu Glu Ser Gly Lys Gly Asp Phe Leu Ile Ile Thr Gly
            675                 680                 685

Pro Asn Met Gly Gly Lys Ser Thr Tyr Ile Arg Gln Val Gly Val Ile
        690                 695                 700

Ser Leu Met Ala Gln Ile Gly Cys Phe Val Pro Cys Glu Glu Ala Glu
705                 710                 715                 720

Ile Ala Ile Val Asp Ala Ile Leu Cys Arg Val Gly Ala Gly Asp Ser
                725                 730                 735

Gln Leu Lys Gly Val Ser Thr Phe Met Val Glu Ile Leu Glu Thr Ala
            740                 745                 750

Ser Ile Leu Lys Asn Ala Ser Lys Asn Ser Leu Ile Ile Val Asp Glu
        755                 760                 765

Leu Gly Arg Gly Thr Ser Thr Tyr Asp Gly Phe Gly Leu Ala Trp Ala
        770                 775                 780

Ile Ala Glu His Ile Ala Ser Lys Ile Gly Cys Phe Ala Leu Phe Ala
785                 790                 795                 800

Thr His Phe His Glu Leu Thr Glu Leu Ser Glu Lys Leu Pro Asn Val
                805                 810                 815

Lys Asn Met His Val Val Ala His Ile Glu Lys Asn Leu Lys Glu Gln
            820                 825                 830
```

```
Lys His Asp Asp Glu Asp Ile Thr Leu Leu Tyr Lys Val Glu Pro Gly
                835                 840                 845

Ile Ser Asp Gln Ser Phe Gly Ile His Val Ala Glu Val Val Gln Phe
    850                 855                 860

Pro Glu Lys Ile Val Lys Met Ala Lys Arg Lys Ala Asn Glu Leu Asp
865                 870                 875                 880

Asp Leu Lys Thr Asn Asn Glu Asp Leu Lys Lys Ala Lys Leu Ser Leu
                885                 890                 895

Gln Glu Val Asn Glu Gly Asn Ile Arg Leu Lys Ala Leu Leu Lys Glu
                900                 905                 910

Trp Ile Arg Lys Val Lys Glu Glu Gly Leu His Asp Pro Ser Lys Ile
    915                 920                 925

Thr Glu Glu Ala Ser Gln His Lys Ile Gln Glu Leu Leu Arg Ala Ile
930                 935                 940

Ala Asn Glu Pro Glu Lys Glu Asn Asp Asn Tyr Leu Lys Tyr Ile Lys
945                 950                 955                 960

Ala Leu Leu Leu

<210> SEQ ID NO 7
<211> LENGTH: 1018
<212> TYPE: PRT
<213> ORGANISM: Saccharomyces cerevisiae S288C

<400> SEQUENCE: 7

Met Ala Gly Gln Pro Thr Ile Ser Arg Phe Phe Lys Lys Ala Val Lys
1               5                   10                  15

Ser Glu Leu Thr His Lys Gln Glu Gln Glu Val Ala Val Gly Asn Gly
                20                  25                  30

Ala Gly Ser Glu Ser Ile Cys Leu Asp Thr Asp Glu Glu Asp Asn Leu
            35                  40                  45

Ser Ser Val Ala Ser Thr Thr Val Thr Asn Asp Ser Phe Pro Leu Lys
50                  55                  60

Gly Ser Val Ser Ser Lys Asn Ser Lys Asn Ser Glu Lys Thr Ser Gly
65                  70                  75                  80

Thr Ser Thr Thr Phe Asn Asp Ile Asp Phe Ala Lys Lys Leu Asp Arg
                85                  90                  95

Ile Met Lys Arg Arg Ser Asp Glu Asn Val Glu Ala Glu Asp Asp Glu
            100                 105                 110

Glu Glu Gly Glu Glu Asp Phe Val Lys Lys Lys Ala Arg Lys Ser Pro
        115                 120                 125

Thr Ala Lys Leu Thr Pro Leu Asp Lys Gln Val Lys Asp Leu Lys Met
130                 135                 140

His His Arg Asp Lys Val Leu Val Ile Arg Val Gly Tyr Lys Tyr Lys
145                 150                 155                 160

Cys Phe Ala Glu Asp Ala Val Thr Val Ser Arg Ile Leu His Ile Lys
                165                 170                 175

Leu Val Pro Gly Lys Leu Thr Ile Asp Glu Ser Asn Pro Gln Asp Cys
            180                 185                 190

Asn His Arg Gln Phe Ala Tyr Cys Ser Phe Pro Asp Val Arg Leu Asn
        195                 200                 205

Val His Leu Glu Arg Leu Val His Asn Leu Lys Val Ala Val Val
210                 215                 220

Glu Gln Ala Glu Thr Ser Ala Ile Lys Lys His Asp Pro Gly Ala Ser
225                 230                 235                 240
```

-continued

Lys Ser Ser Val Phe Glu Arg Lys Ile Ser Asn Val Phe Thr Lys Ala
            245                 250                 255

Thr Phe Gly Val Asn Ser Thr Phe Val Leu Arg Gly Lys Arg Ile Leu
        260                 265                 270

Gly Asp Thr Asn Ser Ile Trp Ala Leu Ser Arg Asp Val His Gln Gly
            275                 280                 285

Lys Val Ala Lys Tyr Ser Leu Ile Ser Val Asn Leu Asn Asn Gly Glu
        290                 295                 300

Val Val Tyr Asp Glu Phe Glu Glu Pro Asn Leu Ala Asp Glu Lys Leu
305                 310                 315                 320

Gln Ile Arg Ile Lys Tyr Leu Gln Pro Ile Glu Val Leu Val Asn Thr
            325                 330                 335

Asp Asp Leu Pro Leu His Val Ala Lys Phe Phe Lys Asp Ile Ser Cys
            340                 345                 350

Pro Leu Ile His Lys Gln Glu Tyr Asp Leu Glu Asp His Val Val Gln
        355                 360                 365

Ala Ile Lys Val Met Asn Glu Lys Ile Gln Leu Ser Pro Ser Leu Ile
        370                 375                 380

Arg Leu Val Ser Lys Leu Tyr Ser His Met Val Glu Tyr Asn Asn Glu
385                 390                 395                 400

Gln Val Met Leu Ile Pro Ser Ile Tyr Ser Pro Phe Ala Ser Lys Ile
            405                 410                 415

His Met Leu Leu Asp Pro Asn Ser Leu Gln Ser Leu Asp Ile Phe Thr
            420                 425                 430

His Asp Gly Gly Lys Gly Ser Leu Phe Trp Leu Leu Asp His Thr Arg
        435                 440                 445

Thr Ser Phe Gly Leu Arg Met Leu Arg Glu Trp Ile Leu Lys Pro Leu
        450                 455                 460

Val Asp Val His Gln Ile Glu Glu Arg Leu Asp Ala Ile Glu Cys Ile
465                 470                 475                 480

Thr Ser Glu Ile Asn Asn Ser Ile Phe Phe Glu Ser Leu Asn Gln Met
            485                 490                 495

Leu Asn His Thr Pro Asp Leu Leu Arg Thr Leu Asn Arg Ile Met Tyr
            500                 505                 510

Gly Thr Thr Ser Arg Lys Glu Val Tyr Phe Tyr Leu Lys Gln Ile Thr
        515                 520                 525

Ser Phe Val Asp His Phe Lys Met His Gln Ser Tyr Leu Ser Glu His
        530                 535                 540

Phe Lys Ser Ser Asp Gly Arg Ile Gly Lys Gln Ser Pro Leu Leu Phe
545                 550                 555                 560

Arg Leu Phe Ser Glu Leu Asn Glu Leu Leu Ser Thr Thr Gln Leu Pro
            565                 570                 575

His Phe Leu Thr Met Ile Asn Val Ser Ala Val Met Glu Lys Asn Ser
            580                 585                 590

Asp Lys Gln Val Met Asp Phe Phe Asn Leu Asn Asn Tyr Asp Cys Ser
        595                 600                 605

Glu Gly Ile Ile Lys Ile Gln Arg Glu Ser Glu Ser Val Arg Ser Gln
        610                 615                 620

Leu Lys Glu Glu Leu Ala Glu Ile Arg Lys Tyr Leu Lys Arg Pro Tyr
625                 630                 635                 640

Leu Asn Phe Arg Asp Glu Val Asp Tyr Leu Ile Glu Val Lys Asn Ser
            645                 650                 655

Gln Ile Lys Asp Leu Pro Asp Asp Trp Ile Lys Val Asn Asn Thr Lys

```
              660                 665                 670
Met Val Ser Arg Phe Thr Thr Pro Arg Thr Gln Lys Leu Thr Gln Lys
                675                 680                 685

Leu Glu Tyr Tyr Lys Asp Leu Leu Ile Arg Glu Ser Glu Leu Gln Tyr
    690                 695                 700

Lys Glu Phe Leu Asn Lys Ile Thr Ala Glu Tyr Thr Glu Leu Arg Lys
705                 710                 715                 720

Ile Thr Leu Asn Leu Ala Gln Tyr Asp Cys Ile Leu Ser Leu Ala Ala
                725                 730                 735

Thr Ser Cys Asn Val Asn Tyr Val Arg Pro Thr Phe Val Asn Gly Gln
                740                 745                 750

Gln Ala Ile Ala Lys Asn Ala Arg Asn Pro Ile Ile Glu Ser Leu
            755                 760                 765

Asp Val His Tyr Val Pro Asn Asp Ile Met Met Ser Pro Glu Asn Gly
        770                 775                 780

Lys Ile Asn Ile Ile Thr Gly Pro Asn Met Gly Gly Lys Ser Ser Tyr
785                 790                 795                 800

Ile Arg Gln Val Ala Leu Leu Thr Ile Met Ala Gln Ile Gly Ser Phe
                805                 810                 815

Val Pro Ala Glu Glu Ile Arg Leu Ser Ile Phe Glu Asn Val Leu Thr
            820                 825                 830

Arg Ile Gly Ala His Asp Asp Ile Ile Asn Gly Asp Ser Thr Phe Lys
        835                 840                 845

Val Glu Met Leu Asp Ile Leu His Ile Leu Lys Asn Cys Asn Lys Arg
    850                 855                 860

Ser Leu Leu Leu Leu Asp Glu Val Gly Arg Gly Thr Gly Thr His Asp
865                 870                 875                 880

Gly Ile Ala Ile Ser Tyr Ala Leu Ile Lys Tyr Phe Ser Glu Leu Ser
                885                 890                 895

Asp Cys Pro Leu Ile Leu Phe Thr Thr His Phe Pro Met Leu Gly Glu
            900                 905                 910

Ile Lys Ser Pro Leu Ile Arg Asn Tyr His Met Asp Tyr Val Glu Glu
        915                 920                 925

Gln Lys Thr Gly Glu Asp Trp Met Ser Val Ile Phe Leu Tyr Lys Leu
    930                 935                 940

Lys Lys Gly Leu Thr Tyr Asn Ser Tyr Gly Met Asn Val Ala Lys Leu
945                 950                 955                 960

Ala Arg Leu Asp Lys Asp Ile Ile Asn Arg Ala Phe Ser Ile Ser Glu
                965                 970                 975

Glu Leu Arg Lys Glu Ser Ile Asn Glu Asp Ala Leu Lys Leu Phe Ser
            980                 985                 990

Ser Leu Lys Arg Ile Leu Lys Ser Asp Asn Ile Thr Ala Thr Asp Lys
        995                 1000                1005

Leu Ala Lys Leu Leu Ser Leu Asp Ile His
    1010                1015

<210> SEQ ID NO 8
<211> LENGTH: 1242
<212> TYPE: PRT
<213> ORGANISM: Saccharomyces cerevisiae

<400> SEQUENCE: 8

Met Ala Pro Ala Thr Pro Lys Ser Lys Thr Ala His Phe Lys Asn
1               5                   10                  15
```

```
Gly Ser Thr Ser Ser Gln Lys Lys Met Lys Gln Ser Ser Leu Leu Ser
                20                  25                  30

Phe Phe Ser Lys Gln Val Pro Ser Gly Thr Pro Ser Lys Lys Val Gln
            35                  40                  45

Lys Pro Thr Pro Ala Thr Leu Glu Asn Thr Ala Thr Asp Lys Ile Thr
50                  55                  60

Lys Asn Pro Glu Gly Gly Lys Thr Gly Lys Leu Phe Val Asp Ala Asp
65                  70                  75                  80

Glu Asp Asn Asp Leu Thr Ile Ala Glu Glu Thr Val Ser Thr Val Arg
                85                  90                  95

Ser Asp Ile Met His Ser Gln Glu Pro Gln Ser Asp Thr Met Leu Asn
            100                 105                 110

Ser Asn Thr Thr Glu Pro Lys Ser Thr Thr Thr Asp Glu Asp Leu Ser
        115                 120                 125

Ser Ser Gln Ser Arg Arg Asn His Lys Arg Arg Leu Asn Tyr Ala Glu
    130                 135                 140

Ser Asp Asp Asp Ser Asp Thr Thr Phe Thr Ala Lys Arg Lys Lys
145                 150                 155                 160

Gly Lys Val Val Asp Ser Glu Ser Asp Glu Asp Glu Tyr Leu Pro Asp
                165                 170                 175

Lys Asn Asp Gly Asp Glu Asp Asp Ile Ala Asp Asp Lys Glu Asp
            180                 185                 190

Ile Lys Gly Glu Leu Ala Glu Asp Ser Gly Asp Asp Asp Leu Ile
        195                 200                 205

Ser Leu Ala Glu Thr Thr Ser Lys Lys Lys Phe Ser Tyr Asn Thr Ser
    210                 215                 220

His Ser Ser Ser Pro Phe Thr Arg Asn Ile Ser Arg Asn Asn Ser Lys
225                 230                 235                 240

Lys Lys Ser Arg Pro Asn Gln Ala Pro Ser Arg Ser Tyr Asn Pro Ser
                245                 250                 255

His Ser Gln Pro Ser Ala Thr Ser Lys Ser Ser Lys Phe Asn Lys Gln
            260                 265                 270

Asn Glu Glu Arg Tyr Gln Trp Leu Val Asp Glu Arg Asp Ala Gln Arg
        275                 280                 285

Arg Pro Lys Ser Asp Pro Glu Tyr Asp Pro Arg Thr Leu Tyr Ile Pro
    290                 295                 300

Ser Ser Ala Trp Asn Lys Phe Thr Pro Phe Glu Lys Gln Tyr Trp Glu
305                 310                 315                 320

Ile Lys Ser Lys Met Trp Asp Cys Ile Val Phe Phe Lys Lys Gly Lys
                325                 330                 335

Phe Phe Glu Leu Tyr Glu Lys Asp Ala Leu Leu Ala Asn Ala Leu Phe
            340                 345                 350

Asp Leu Lys Ile Ala Gly Gly Arg Ala Asn Met Gln Leu Ala Gly
        355                 360                 365

Ile Pro Glu Met Ser Phe Glu Tyr Trp Ala Ala Gln Phe Ile Gln Met
    370                 375                 380

Gly Tyr Lys Val Ala Lys Val Asp Gln Arg Glu Ser Met Leu Ala Lys
385                 390                 395                 400

Glu Met Arg Glu Gly Ser Lys Gly Ile Val Lys Arg Glu Leu Gln Cys
                405                 410                 415

Ile Leu Thr Ser Gly Thr Leu Thr Asp Gly Asp Met Leu His Ser Asp
            420                 425                 430

Leu Ala Thr Phe Cys Leu Ala Ile Arg Glu Glu Pro Gly Asn Phe Tyr
```

```
                435                 440                 445
Asn Glu Thr Gln Leu Asp Ser Ser Thr Ile Val Gln Lys Leu Asn Thr
    450                 455                 460
Lys Ile Phe Gly Ala Ala Phe Ile Asp Thr Ala Thr Gly Glu Leu Gln
465                 470                 475                 480
Met Leu Glu Phe Glu Asp Asp Ser Glu Cys Thr Lys Leu Asp Thr Leu
                    485                 490                 495
Met Ser Gln Val Arg Pro Met Glu Val Val Met Glu Arg Asn Asn Leu
                500                 505                 510
Ser Thr Leu Ala Asn Lys Ile Val Lys Phe Asn Ser Ala Pro Asn Ala
                515                 520                 525
Ile Phe Asn Glu Val Lys Ala Gly Glu Glu Phe Tyr Asp Cys Asp Lys
                530                 535                 540
Thr Tyr Ala Glu Ile Ile Ser Ser Glu Tyr Phe Ser Thr Glu Glu Asp
545                 550                 555                 560
Trp Pro Glu Val Leu Lys Ser Tyr Tyr Asp Thr Gly Lys Lys Val Gly
                    565                 570                 575
Phe Ser Ala Phe Gly Gly Leu Leu Tyr Tyr Leu Lys Trp Leu Lys Leu
                580                 585                 590
Asp Lys Asn Leu Ile Ser Met Lys Asn Ile Lys Glu Tyr Asp Phe Val
                595                 600                 605
Lys Ser Gln His Ser Met Val Leu Asp Gly Ile Thr Leu Gln Asn Leu
610                 615                 620
Glu Ile Phe Ser Asn Ser Phe Asp Gly Ser Asp Lys Gly Thr Leu Phe
625                 630                 635                 640
Lys Leu Phe Asn Arg Ala Ile Thr Pro Met Gly Lys Arg Met Met Lys
                    645                 650                 655
Lys Trp Leu Met His Pro Leu Leu Arg Lys Asn Asp Ile Glu Ser Arg
                660                 665                 670
Leu Asp Ser Val Asp Ser Leu Leu Gln Asp Ile Thr Leu Arg Glu Gln
                675                 680                 685
Leu Glu Ile Thr Phe Ser Lys Leu Pro Asp Leu Glu Arg Met Leu Ala
                690                 695                 700
Arg Ile His Ser Arg Thr Ile Lys Val Lys Asp Phe Glu Lys Val Ile
705                 710                 715                 720
Thr Ala Phe Glu Thr Ile Ile Glu Leu Gln Asp Ser Leu Lys Ser Asn
                    725                 730                 735
Asp Leu Lys Gly Asp Val Ser Lys Tyr Ile Ser Ser Phe Pro Glu Gly
                740                 745                 750
Leu Val Glu Ala Val Lys Ser Trp Thr Asn Ala Phe Glu Arg Gln Lys
                755                 760                 765
Ala Ile Asn Glu Asn Ile Ile Val Pro Gln Arg Gly Phe Asp Ile Glu
                770                 775                 780
Phe Asp Lys Ser Met Asp Arg Ile Gln Glu Leu Glu Asp Glu Leu Met
785                 790                 795                 800
Glu Ile Leu Met Thr Tyr Arg Lys Gln Phe Lys Cys Ser Asn Ile Gln
                    805                 810                 815
Tyr Lys Asp Ser Gly Lys Glu Ile Tyr Thr Ile Glu Ile Pro Ile Ser
                820                 825                 830
Ala Thr Lys Asn Val Pro Ser Asn Trp Val Gln Met Ala Ala Asn Lys
                835                 840                 845
Thr Tyr Lys Arg Tyr Tyr Ser Asp Glu Val Arg Ala Leu Ala Arg Ser
                850                 855                 860
```

Met Ala Glu Ala Lys Glu Ile His Lys Thr Leu Glu Asp Leu Lys
865                 870                 875                 880

Asn Arg Leu Cys Gln Lys Phe Asp Ala His Tyr Asn Thr Ile Trp Met
            885                 890                 895

Pro Thr Ile Gln Ala Ile Ser Asn Ile Asp Cys Leu Leu Ala Ile Thr
        900                 905                 910

Arg Thr Ser Glu Tyr Leu Gly Ala Pro Ser Cys Arg Pro Thr Ile Val
            915                 920                 925

Asp Glu Val Asp Ser Lys Thr Asn Thr Gln Leu Asn Gly Phe Leu Lys
930                 935                 940

Phe Lys Ser Leu Arg His Pro Cys Phe Asn Leu Gly Ala Thr Thr Ala
945                 950                 955                 960

Lys Asp Phe Ile Pro Asn Asp Ile Glu Leu Gly Lys Glu Gln Pro Arg
            965                 970                 975

Leu Gly Leu Leu Thr Gly Ala Asn Ala Ala Gly Lys Ser Thr Ile Leu
        980                 985                 990

Arg Met Ala Cys Ile Ala Val Ile Met Ala Gln Met Gly Cys Tyr Val
            995                 1000                1005

Pro Cys Glu Ser Ala Val Leu Thr Pro Ile Asp Arg Ile Met Thr
    1010                1015                1020

Arg Leu Gly Ala Asn Asp Asn Ile Met Gln Gly Lys Ser Thr Phe
    1025                1030                1035

Phe Val Glu Leu Ala Glu Thr Lys Lys Ile Leu Asp Met Ala Thr
    1040                1045                1050

Asn Arg Ser Leu Leu Val Val Asp Glu Leu Gly Arg Gly Gly Ser
    1055                1060                1065

Ser Ser Asp Gly Phe Ala Ile Ala Glu Ser Val Leu His His Val
    1070                1075                1080

Ala Thr His Ile Gln Ser Leu Gly Phe Ala Thr His Tyr Gly
    1085                1090                1095

Thr Leu Ala Ser Ser Phe Lys His His Pro Gln Val Arg Pro Leu
    1100                1105                1110

Lys Met Ser Ile Leu Val Asp Glu Ala Thr Arg Asn Val Thr Phe
    1115                1120                1125

Leu Tyr Lys Met Leu Glu Gly Gln Ser Glu Gly Ser Phe Gly Met
    1130                1135                1140

His Val Ala Ser Met Cys Gly Ile Ser Lys Glu Ile Ile Asp Asn
    1145                1150                1155

Ala Gln Ile Ala Ala Asp Asn Leu Glu His Thr Ser Arg Leu Val
    1160                1165                1170

Lys Glu Arg Asp Leu Ala Ala Asn Asn Leu Asn Gly Glu Val Val
    1175                1180                1185

Ser Val Pro Gly Gly Leu Gln Ser Asp Phe Val Arg Ile Ala Tyr
    1190                1195                1200

Gly Asp Gly Leu Lys Asn Thr Lys Leu Gly Ser Gly Glu Ala Val
    1205                1210                1215

Leu Asn Tyr Asp Trp Asn Ile Lys Arg Asn Val Leu Lys Ser Leu
    1220                1225                1230

Phe Ser Ile Ile Asp Asp Leu Gln Ser
    1235                1240

<210> SEQ ID NO 9
<211> LENGTH: 209

<212> TYPE: PRT
<213> ORGANISM: Saccharomyces cerevisiae S288C

<400> SEQUENCE: 9

Met Ala Pro Ser Ile Ala Thr Val Lys Ile Ala Arg Asp Met Val Leu
1               5                   10                  15

Pro Leu Arg Ile Phe Val Asn Arg Lys Gln Ile Leu Gln Thr Asn Asp
            20                  25                  30

Lys Thr Ser Asn Lys Ser Asn Ala Thr Ile Phe Glu Ala Pro Leu Leu
        35                  40                  45

Ser Asn Asn Ser Ile Ile Cys Leu Lys Ser Pro Asn Thr Arg Ile Tyr
    50                  55                  60

Leu Ser Gln Gln Asp Lys Lys Asn Leu Cys Asp Glu Ile Lys Glu Asp
65                  70                  75                  80

Leu Leu Leu Ile Val Tyr Glu Leu Ala Ser Pro Glu Ile Ile Ser Ser
                85                  90                  95

Val Leu Ser Lys Ile Arg Val Gly His Ser Thr Asp Phe Gln Ile Asn
            100                 105                 110

Val Leu Pro Lys Leu Phe Ala Gly Ala Asp Thr Asp Asn Ala Val Thr
        115                 120                 125

Ser His Ile Gln Ser Val Thr Arg Leu Ala Lys Phe Lys Tyr Lys Leu
    130                 135                 140

His Tyr Lys His Lys Trp Glu Leu Asp Ile Phe Ile Asn Ser Ile Lys
145                 150                 155                 160

Lys Ile Ala Asn Leu Arg His Tyr Leu Met Phe Gln Thr Leu Thr Leu
                165                 170                 175

Asn Gly Phe Ser Leu Asn Ala Gly Pro Lys Thr Leu Leu Ala Arg Lys
            180                 185                 190

Ile Glu Lys Gln Pro Gln Val Pro Asn Leu Leu Ile Glu Asn Gly Asp
        195                 200                 205

Ala

<210> SEQ ID NO 10
<211> LENGTH: 231
<212> TYPE: PRT
<213> ORGANISM: Homo sapiens

<400> SEQUENCE: 10

Met Phe Ile Leu Thr Pro Lys Leu Gln Ile Pro Ala Thr Phe Asp Gly
1               5                   10                  15

Met Ala Asn Val Lys Ala Ala Pro Lys Ile Ile Asp Thr Gly Gly Gly
            20                  25                  30

Phe Ile Leu Glu Glu Glu Glu Glu Glu Gln Lys Ile Gly Lys Val
        35                  40                  45

Val His Gln Pro Gly Pro Val Met Glu Phe Asp Tyr Val Ile Cys Glu
    50                  55                  60

Glu Cys Gly Lys Glu Phe Met Asp Ser Tyr Leu Met Asn His Phe Asp
65                  70                  75                  80

Leu Pro Thr Cys Asp Asn Cys Arg Asp Ala Asp Lys His Lys Leu
                85                  90                  95

Ile Thr Lys Thr Glu Ala Lys Gln Glu Tyr Leu Leu Lys Asp Cys Asp
            100                 105                 110

Leu Glu Lys Arg Glu Pro Pro Leu Lys Phe Ile Val Lys Lys Asn Pro
        115                 120                 125

His His Ser Gln Trp Gly Asp Met Lys Leu Tyr Leu Lys Leu Gln Ile

```
                130                 135                 140
Val Lys Arg Ser Leu Glu Val Trp Gly Ser Gln Glu Ala Leu Glu Glu
145                 150                 155                 160

Ala Lys Glu Val Arg Gln Glu Asn Arg Glu Lys Met Lys Gln Lys Lys
                165                 170                 175

Phe Asp Lys Lys Val Lys Glu Leu Arg Arg Ala Val Arg Ser Ser Val
            180                 185                 190

Trp Lys Arg Glu Thr Ile Val His Gln His Glu Tyr Gly Pro Glu Glu
            195                 200                 205

Asn Leu Glu Asp Asp Met Tyr Arg Lys Thr Cys Thr Met Cys Gly His
            210                 215                 220

Glu Leu Thr Tyr Glu Lys Met
225                 230
```